(12) United States Patent
Lawie et al.

(10) Patent No.: US 10,393,436 B2
(45) Date of Patent: Aug. 27, 2019

(54) DRYING APPARATUS AND RELATED METHOD

(71) Applicant: MINEX CRC LTD

(72) Inventors: David Charles Lawie, Woodlands (AU); Anthony Malcolm Stevens, Mullaloo (AU); Frederick Allan Blaine, Doubleview (AU)

(73) Assignee: MINEX CRC LTD, Kensington, Western Australia (AU)

( * ) Notice: Subject to any disclaimer, the term of this patent is extended or adjusted under 35 U.S.C. 154(b) by 207 days.

(21) Appl. No.: 15/528,377

(22) PCT Filed: Nov. 19, 2015

(86) PCT No.: PCT/AU2015/000701
§ 371 (c)(1),
(2) Date: May 19, 2017

(87) PCT Pub. No.: WO2016/077870
PCT Pub. Date: May 26, 2016

(65) Prior Publication Data
US 2017/0363353 A1    Dec. 21, 2017

(30) Foreign Application Priority Data

Nov. 19, 2014  (AU) ................................ 2014904649

(51) Int. Cl.
*F26B 1/00* (2006.01)
*F26B 3/08* (2006.01)
(Continued)

(52) U.S. Cl.
CPC ............... *F26B 21/10* (2013.01); *F26B 3/08* (2013.01); *F26B 17/00* (2013.01); *F26B 17/10* (2013.01);
(Continued)

(58) Field of Classification Search
CPC .. F26B 21/10; F26B 17/00; F26B 3/08; F26B 17/10; F26B 17/107; F26B 1/005; G01N 1/44

See application file for complete search history.

(56) References Cited

U.S. PATENT DOCUMENTS

| 2,316,207 A | 4/1943 | Winter |
| 4,594,793 A | 6/1986 | Carlson |

(Continued)

FOREIGN PATENT DOCUMENTS

| CN | 2919228 Y | 7/2007 |
| CN | 101435752 A | 5/2009 |

(Continued)

OTHER PUBLICATIONS

European Search Report and Written Opinion issued in PCT/AU2015000701, dated Jul. 6, 2018.
(Continued)

*Primary Examiner* — Jessica Yuen
(74) *Attorney, Agent, or Firm* — Stites & Harbison, PLLC; Terry L. Wright

(57) ABSTRACT

There is provided an apparatus for use in drying a sample of geological material having a substantial moisture content. In one aspect, the apparatus comprises a means for providing a flow of heated fluid, and a means for managing the thermal state of the flow of heated fluid. The means for managing the thermal state of the flow of heated fluid is arranged operable with the means for providing a flow of heated fluid so that exposure of the sample to the flow of heated fluid facilitates a reduction of the moisture content of a portion of the sample while substantially preserving one or more chemical and/or physical properties of the portion.

17 Claims, 11 Drawing Sheets

(51) Int. Cl.
  *G01N 1/44*  (2006.01)
  *F26B 17/00* (2006.01)
  *F26B 17/10* (2006.01)
  *F26B 21/10* (2006.01)
(52) U.S. Cl.
  CPC .............. *F26B 17/107* (2013.01); *G01N 1/44* (2013.01); *F26B 1/005* (2013.01)

(56) References Cited

U.S. PATENT DOCUMENTS

| 2003/0080224 | A1 | 5/2003 | Rowley |
| 2006/0035192 | A1 | 2/2006 | Coles et al. |
| 2008/0264013 | A1 | 10/2008 | Rowley et al. |

FOREIGN PATENT DOCUMENTS

| JP | 2006112710 A | 4/2006 |
| JP | 2006266552 A | 10/2006 |
| RU | 2425311 C1 | 7/2011 |
| RU | 2480693 C2 | 4/2013 |
| WO | WO-88/04020 A1 | 6/1988 |
| WO | WO-1992/012796 A1 | 8/1992 |
| WO | WO-2011/009457 A1 | 1/2011 |
| WO | WO-2014/169319 A1 | 10/2014 |

OTHER PUBLICATIONS

First Examination Report for Chilean Patent Application 01291-2017 dated Jul. 17, 2018.
Letter from Chilean associate dated Aug. 3, 2018 reporting on the First Examination Report for Chilean Patent Application 01291-2017.
International Search Report and Written Opinion of the International Searching Authority issued in PCT/AU2015/000701, dated Dec. 22, 2015; ISA/AU.
International Preliminary Report on Patentability for PCT/AU2015/000701, IPEA/AU, completed Dec. 15, 2016.

DRYING APPARATUS AND RELATED METHOD

CROSS-REFERENCE TO RELATED APPLICATIONS

This application is a 371 U.S. National Stage of International Application No. PCT/AU2015/000701, filed Nov. 19, 2015, and published in English as WO 2016/077870 A1 on May 26, 2016, which claims the benefit of and priority to Australian Patent Application No. 2014904649, filed Nov. 19, 2014. The entire disclosures of the above applications are incorporated herein by reference.

TECHNICAL FIELD

An apparatus and related method for drying geological material is disclosed.

The present application claims priority to Australian provisional patent application No 2014904649, the content of which is incorporated herein.

BACKGROUND ART

The following discussion of the background art is intended to facilitate an understanding of the present invention only. The discussion is not an acknowledgement or admission that any of the material referred to is or was part of the common general knowledge as at the priority date of the application.

Third parties have proposed various apparatus and associated methodologies for preparing particulate matter for subsequent particle analysis. However, conventional techniques for preparing samples destined for quasi in-situ spectrometric analysis have been found to be generally too slow and do not provide an acceptable free flowing powder without subsequent processing being required.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

It is against this background that the present invention has been developed.

SUMMARY OF INVENTION

According to a first principal aspect, there is provided an apparatus for use in drying a sample of geological material having a substantial moisture content, the apparatus comprising:

means for providing a flow of heated fluid; and means for managing a thermal state of the flow of heated fluid, said means arranged operable with the means for providing a flow of heated fluid so that exposure of the sample to the flow of heated fluid facilitates a reduction of the moisture content of a portion of the sample while substantially preserving one or more chemical and/or physical properties of the portion.

Typically, material for which the apparatus of the present principal aspect relates includes geological samples of a generally particulate nature having been extracted in natural or 'raw' form directly from a predetermined location, such as for example a remote geographical site or location of interest for drilling or like activities, for subsequent spectrometric processing/analysis which is conducted on-site. Accordingly, material sourced in this manner generally harbours a substantial amount of moisture. Such geological samples may contain a number of constituent materials, the identity of which is one of a number of potential objectives for subsequent processing/analysis. It will therefore be understood that the principles of the principal aspects described herein could be readily applied to any geological material having a substantial moisture content, and thus should not be interpreted so as to be restricted to material specifically extracted in raw or natural form.

As noted, as the samples of material are generally extracted directly from a predetermined geological site, they can typically harbour a substantial amount of moisture (which can also be due to the extraction process used). As part of subsequent process/analysis, the sample(s) need to be dried in accordance with an appropriate drying profile. However, the drying of the sample must be such so as to reduce or avoid damaging the inherent signature chemical and/or physical characteristic properties or mineralogy of each constituent material present in the sample. For example, rapid drying of such samples brings with it a significant problem in that exceeding certain temperature thresholds has the potential to cause constituents in the molecular composition to change state, thereby risking the integrity of the molecular structure of the sample when undergoing mineral analysis.

Embodiments of the first principal aspect, and those described below, may serve to provide the advantage of allowing for substantially rapid or expeditious drying of geological materials while maintaining sufficiently low temperatures so as to reduce or avoid the risk of compromising the mineralogy of the constituents in the material sample. In at least one embodiment, operation of the apparatus serves to produce a disagglomerated or disaggregated free flowing powder of high mineralogical integrity for analysis purposes.

Embodiments of the apparatus of the present principal aspect may serve to provide smaller scale arrangements which are readily portable and/or realise relatively lower build and/or maintenance costs. In at least one sense, the reduced scale that embodiments of the apparatus of the present aspect are able to adopt is not achievable using larger industrial scale arrangements in that such large scale industrial systems are generally used for continuous drying of homogeneous material where the preservation of the integrity of a batch of the material is not of substantive concern during the drying process. Embodiments of the present apparatus may serve to provide small scale field portable configurations which allow for rapid/expeditious drying of sample material while preserving the minerology of the constituents in the sample portion of material is achievable in batch form (ie. allowing for drying of sample material in discrete batches). In this manner, rather than operating on a continuous feed basis, the thermal environment of the apparatus can be balanced appropriately with respect to the quantity or size of the material input or exposed to the heated fluid flow, allowing management of the environment to be appropriate for achieving an acceptable result—drying within an acceptable time frame and of acceptable form (ie. preferably of a disagglomerated or disaggregated free flowing powder). In one embodiment, the thermal environment provided by the apparatus can be optimised for the specific size of the sample of material to be dried.

In one embodiment, the apparatus is configured so as to dry the geological material in an expeditious manner so that subsequent processing/analysis of the dried material can be commensurate with a time scale as near to real-time as possible. In at least one sense, embodiments of the apparatus may serve to allow for a more rapid and in-field application of proper sampling techniques. Thus, in one arrangement, the means for providing a flow of heated fluid and the means for managing the thermal state of the heated fluid flow are arranged operable for providing rapid or expeditious drying of the portion.

In one embodiment, the means for providing a flow of heated fluid and the means for managing the thermal state of the heated fluid flow are arranged operable so as to facilitate a substantial reduction of the moisture content of the portion of the sample to below or about a predetermined level while substantially preserving one or more chemical and/or physical properties of the sample portion.

In another embodiment, the means for providing a flow of heated fluid and the means for managing the thermal state of the heated fluid flow are arranged operable so as to facilitate a substantial reduction of the moisture content of the portion of the sample while the temperature of the portion remains substantially below a predetermined temperature level so as to substantially preserve one or more chemical and/or physical properties of the sample portion.

In one embodiment, the means for providing a flow of heated fluid is operable for facilitating a reduction of the moisture content of the portion of the sample to below or about a predetermined level within a predetermined time period. The predetermined time period may be from about 2 minutes to 5 minutes, or from about 2 minutes to about 3 minutes.

In one embodiment, the apparatus comprises a passage having a longitudinal axis and through which the heated fluid flows from an upstream end to or toward an end downstream thereof.

In one arrangement, the means for providing a flow of heated fluid is arranged operable with a heat source, the heat source being arranged so that heated fluid can be introduced into the passage in a tangential manner.

In one embodiment, the means for providing a flow of heated fluid comprises a fluid distribution assembly, the fluid distribution assembly being configured for providing a flow of heated fluid through the passage.

In another embodiment, the fluid distribution assembly is arranged for facilitating, at least in part, a portion of the heated fluid to flow substantially about an axis of the passage.

In one embodiment, the fluid distribution assembly is configured operable with a heat source configured for heating fluid.

In one embodiment, the heat source is provided in the form of a heating element, such as, for example, an in-line heating element operably associated with a temperature controller. In this manner, and in at least one operable arrangement, heated airflow can be assisted by the use of a fluid driving means, such as for example, a fan unit or a vacuum unit provided downstream of the heat source. It will be appreciated that air is preferably filtered before entering the system.

In one embodiment, the predetermined temperature level is below or about 105 degrees Celsius.

In another embodiment, the predetermined temperature level is below or about 100 degrees Celsius.

In one embodiment, the temperature of the heated flow of fluid is managed so as to be below about 105 degrees Celsius. In this manner, the temperature of the sample of material dried is below about 105 degrees Celsius. In some situations, lower temperatures might be preferable/suitable for achieving acceptable drying rates depending the circumstances to hand.

In one embodiment, the passage is defined by a chamber of cylindrical form, having a circular cross section substantially uniform along its length. In such embodiments, an interior wall of the chamber, and the chamber's own longitudinal axis, are aligned substantially concentric about the longitudinal axis of the passage.

In one embodiment, the longitudinal axis of the chamber is aligned substantially in the vertical plane. In this arrangement, the upstream end of the chamber is lowermost, and the downstream end of the chamber is uppermost. Thus, it will be understood that the intended flow of the heated fluid in this arrangement is substantially against the action of gravity.

In one embodiment, the volumetric capacity of the chamber is configured of a size appropriate for the quantity of the sample material input into the chamber, a relationship between the volumetric capacity of the chamber and the quantity of material serving to assist in the management of the thermal state of the flow of heated fluid for drying purposes. Prototype embodiments suggest that the volumetric capacity of the chamber assists, at least in part, in providing a thermal environment which can be managed in order to reduce or avoid the risk of compromising the integrity of the mineralogy of the constituents of the sample when seeking to reduce the drying time. In some arrangements, it is considered that a relatively smaller volumetric capacity (as compared with large scale flash drying devices used for industrial purposes) is advantageous in providing a generally forgiving thermal environment for expeditious drying purposes. In one embodiment, the volumetric size of the chamber is optimised for the specific size of the sample of material to be dried.

In one embodiment, the volumetric capacity of the chamber is configured of a size appropriate for a quantity of the sample material input into the chamber for drying the input sample material for achieving an acceptable level of moisture content in the dried sample material within an acceptable period of time.

In one embodiment, the chamber is provided having a volumetric capacity in the order of about 4,000 cubic centimeters. The inventors have found that a chamber having a volumetric capacity of this order allows small or discrete amounts of sample material to be dried in the desired manner while maintaining sample integrity, and allowing for portability of the apparatus.

In one embodiment, the apparatus comprises an input means configured operable for introducing sample material to be dried into the flow of heated fluid (by way of, for example, the passage/chamber) for drying purposes, the sample material being introduced into the flow of heated fluid in a discrete manner. In one form, the input means is provided in the form of a feed assembly configured for receiving a portion of the sample material and arranged relative to the chamber so that the received portion of sample material may become exposed to the heated fluid.

In one embodiment, the input means is provided in the form of, for example, a plunger/capsule type configuration. In another embodiment, the input means is provided in the form of, for example, an auger feeding unit.

In another embodiment, the interior wall of the chamber is provided or lined with a non-stick material such as for example, polytetrafluoroethylene (ie. Teflon), to reduce material retention in the chamber and maintain sample integrity. It will be appreciated that any such material is preferably also thermally stable.

In one embodiment, the downstream end of the passage is arranged in fluid communication (by way of, for example, a conduit) with a collection means so that dried material can be collected thereby for subsequent processing/analysis. In one embodiment, the collection means is configured operable in a cyclonic like manner.

In one embodiment, the fluid distribution assembly comprises a means for establishing a region of low pressure downstream of the heat source so as to, at least in part, facilitate or encourage the flow of the heated fluid and/or carriage of dried material through the passage/chamber and toward the collections means. In one embodiment, the means for establishing the region of low pressure may comprise a venturi unit or vacuum unit provided downstream of the collection means.

In one embodiment, the collections means may itself comprise a means for establishing a region of low pressure downstream of the heat source, such as for example a vacuum unit, for assisting in drawing out material carried by the flow of heated fluid.

In another embodiment, the collections means comprises a collection receptacle within which dried material may be collected.

In one embodiment, the apparatus may include a classifying means (provided, for example, in the form of a classifier assembly) arranged in operable association with the collection means so that dried material may be separated into specific predetermined portions or size ranges of material. In one embodiment, classification of the dried material can be by way of a conventional classifier unit (eg. a rotating classifier).

In another embodiment, the fluid distribution assembly comprises a fluid mixing assembly configured for facilitating, at least in part, rotational, non-linear, or unsteady flow of the fluid as it progresses downstream.

In one embodiment, the fluid distribution assembly comprises a fluid mixing assembly configured for engaging fluid passing thereby for, at least in part, facilitating fluidic mixing within the fluid. In this manner, it will be understood that engagement or interaction of the passing fluid by the fluid mixing assembly serves to provoke or facilitate, at least in part, rotational, non-linear, or unsteady flow of the fluid as it progresses downstream. In some arrangements, such provocation/facilitation may be by way of non-linear localised flow such as for example, localised eddy currents.

In one embodiment, fluid heated by the heat source is directed in such a manner so that it may be engaged by the fluid mixing assembly so as to assist in the development of the rotational flow of heated fluid through the passage/chamber.

In another embodiment, the apparatus comprises a disaggregation means arranged in operable association with fluid distribution assembly, the disaggregation means configured operable for engaging with sample material to be dried for the purpose of modifying (such as for example, breaking down the material) the sample material for increasing the effective surface area of the sample material exposed to the heated fluid flow.

In another arrangement, the disaggregation means is operable for processing materials that are already of fine form, but which may tend to be aggregated when wet and/or aggregate on drying.

In one arrangement, the disaggregation means is provided in the form of a disaggregation assembly.

In another embodiment, the disaggregation assembly is provided upstream of the input means.

In a further embodiment, the fluid distribution assembly comprises a means by which fluid heated by the heat source is caused to be moved or directed so as to engage with the fluid mixing assembly. In one embodiment, movement or direction of the heated fluid toward the fluid mixing assembly may be achieved by way of a fan unit configured so as to direct (or blow) heated fluid toward the fluid mixing assembly for engagement thereby.

In one arrangement, the heat source may comprise a fan unit which is arranged to direct heated fluid toward the fluid mixing assembly. In a simplified form, the heat source and the fan may be an integrated component provided in the form of, for example, a heat gun.

In one embodiment, the fluid mixing assembly comprises a rotating member such as for example an impeller. The rotating member may be configured so as to promote mixing, or multiple unsteady local eddying motions, within the heated fluid.

In one embodiment, the rotating member comprises a body having one or more fluid engaging members such as, for example, fins or protrusions extending outwardly from the body. The or each fluid engaging member may be shaped or configured so as to engage with the oncoming or passing fluid while rotating so as to promote, at least in part, unsteady fluid flow. Thus, the shape or profile of the or each fluid engaging member may be configured in accordance with one which seeks to promote fluidic mixing (or unsteady local eddy motion).

In one embodiment, the rotating member is positioned and configured to operate within an upstream end of the chamber. In such arrangements, the rotating member is positioned such that it operates or rotates within a plane which is aligned substantially transverse to the longitudinal axis of the passage/chamber (ie. the axis about which the rotating member rotates is aligned concentric with the longitudinal axis of the chamber/passage). In at least one arrangement, one or more of the protrusions extends generally in the downstream direction.

In some embodiments, the rotating member is arranged to be driven by a prime mover by way of a drive coupling means configured to transfer rotational drive provided by the prime mover to the rotating member. The prime mover may include any means capable of providing rotational drive, such as for example, an electric motor. The drive coupling means may be direct or indirect (ie. a belt drive).

In one embodiment, the rotating member of the fluid mixing assembly is operable for rotating at a rate between about 15,000 to about 25,000 revolutions per minute.

In another embodiment, the rotating member of the fluid mixing assembly is operable for rotating at about 22,000 revolutions per minute.

The fluid mixing assembly, the heat source, and the means for directing heated fluid, may be arranged relative one another such that heated fluid engages the rotating member at or near a periphery of the rotating member. In one embodiment, the heated fluid engages the rotating member from upstream thereof.

In one embodiment, the fluid engaging members or protrusions of the rotating member are configured so as to be readily capable of engaging portions of material introduced into the flow of heated fluid within the chamber by the input means.

In another embodiment, the fluid mixing assembly is operable, at least in part, for engaging input sample material to be dried into the chamber for breaking the material down for increasing the surface area of the material which is exposed to the thermal environment for drying purposes.

In one embodiment, the fluid mixing assembly and the disaggregation assembly are substantially the same component. For example, in one embodiment, the fluid mixing assembly and the disaggregation means may be provided as an integrated component/assembly. In this manner, it will be understood that the integrated fluid mixing/disaggregation assembly serves at least two purposes: (1) assisting in facilitating or provoking the introduction of rotational or unsteady flow components into the flow of heated fluid, and (2) breaking up material introduced into the chamber for drying so as to increase the effective surface area of the material which is exposed to the thermal environment for drying purposes and/or disaggregating any material which may aggregate during the drying process.

In one embodiment, the rotating member of the fluid mixing assembly is operable for rotating at a rate between about 15,000 to about 25,000 revolutions per minute, the rate of rotation operable for at least:
 (i) promoting or facilitating, at least in part, rotational, non-linear, or unsteady flow of the fluid as it progresses downstream; and/or
 (ii) engaging with sample material to be dried for the purpose of modifying the sample for increasing the effective surface area of the sample material which is exposed to the heated fluid flow.

In one embodiment, the fluid mixing assembly is provided upstream of the input means. In this manner, when the chamber is aligned with the vertical plane, material input by way of the input means may fall upstream toward the fluid mixing assembly under the influence of gravity.

In one embodiment, the heat source and means by which heated fluid is directed for engagement by the fluid mixing assembly is arranged upstream of the rotating member.

In one arrangement, the heat source is arranged so that heated fluid can be introduced into the passage in a tangential manner. In a further embodiment, the means by which heated fluid is directed for engagement by the fluid mixing assembly is configured so as to direct or inject heated fluid into the passage/chamber in a tangential manner.

In one arrangement, the heating element is arranged relative to the chamber so that heated fluid may be introduced/directed/injected into the chamber upstream of the rotating member, and in a direction such that the heated fluid enters the chamber substantially tangential thereto. In one embodiment, the heated fluid is introduced or directed across an internal surface of the chamber wall prior to it engaging with the rotating member.

In another arrangement, the heat source (eg. heating element) is arranged relative a manifold assembly so that heated fluid may be communicated from the heat source into the passage/chamber along a path which is substantially tangential to the chamber.

It will be appreciated that the tangential introduction/injection of the heated fluid serves to, at least in part, introduce a component of angular or rotational motion into the heated flow of fluid as it enters the chamber. It will be understood that this is due to the fluid being directed across the internal wall of the chamber, the shape of the internal wall serving to impart an angular or rotational component of motion into the flow—in contrast to a flow which is purely axial along the longitudinal axis of the passage/chamber. This rotational or angular flow of heated fluid then engages the fluid mixing assembly where the fins or protrusions of the rotating member act upon the fluid to, at least in part, further encourage and/or promote a generally unsteady flow through the passage/chamber. The presence of a rotational and/or unsteady flow is considered advantageous in ensuring sufficient exposure of the sample of material for drying purposes. In one arrangement, the direction of rotation of the fluid is the same direction that the impeller of the fluid mixing assembly rotates.

It will be appreciated that the developed flow could be turbulent, or substantially curvilinear in nature. In some embodiments, a helical or vortex flow aligned substantially relative to the longitudinal axis of the passage/chamber is sought. An advantage of providing a path of flow which is other than purely axial is that the period of exposure to the heated flow is increased as the path is generally longer for the same volumetric flow velocity.

In embodiments where the chamber is vertically aligned and operable with a vacuum source, movement of heated fluid within the chamber (eg. the heated fluid rising in the chamber) and flow through the passage is by way of the lower pressure created downstream of the chamber by the vacuum source. Due in part to the operation of the fluid mixing/disaggregation assembly, the path of the flow of heated fluid is generally rotational in nature as it travels downstream. In operation, sufficiently dried particulate reduces to a weight that allows it to be carried by the moving fluid out from the chamber for collection. Material not sufficiently dry will tend to fall by way of gravity toward the lowermost end of the chamber from which the heated air stream emanates from. If while falling the material is sufficiently exposed to the heated flow and dries, its weight may reduce to the point where it will be carried by the flow to the collection means. If not sufficiently dry, the material will continue to fall toward the upstream end of the chamber.

Additionally, larger particles or agglomerates may fall by way of gravity. The dryness of the sample material may, in some instances, likely not control whether the sample material falls or not. If the dried sample is sufficiently fine, it will flow through the system whether dry or not, but the rate of drying will be sufficiently high so that the sample material is dry by the time it is collected in the collection means (or when leaving the chamber). Wetter sample material may tend to become agglomerated more readily meaning that larger heavier particles may be less influenced by the air flow.

Following from the above, non-sufficiently dry material may ultimately make contact with the rotating member. In this event, the centripetal forces developed by the rotating member will serve to cause the still moisture laden material to be directed radially outward from the centre axis of the rotating member and toward the periphery of the chamber where the flow of heated fluid engages the protrusions of the rotating member for mixing purposes. Thus, moisture laden material is again exposed to the flow of heated fluid for drying. If not sufficiently dried as a result of the reiterated exposure, the material will again fall and contact the rotating member, where it will again be directed to the periphery of the rotating member to commence a further iteration of exposure to the oncoming flow of heated fluid.

It will be appreciated that contact with the rotating member and its protrusions by the falling material serves, at least in part, to break the sample(s) of material up into smaller portions so as to increase the effective surface area for drying purposes. In one embodiment, the reduction in size of a sample of material to be dried can be conducted in the form of disaggregation of aggregated smaller portions or particles of the sample or comminution of substantially larger portions or particles of said sample.

In one embodiment, the fluid mixing assembly is arranged so as to be movable in a direction substantially aligned with the longitudinal axis of the passage/chamber for, at least in part, modifying and/or controlling the flow of heated fluid. In another arrangement, the rotating member is configured movable in a direction substantially aligned with the longitudinal axis of the passage/chamber. In this manner, the axial position of the rotating member is adjustable relative to the chamber.

In another embodiment, the region of the chamber within which the rotating member of the fluid mixing assembly operates comprises a shaped annular wall. In such arrangements, a surface portion of the shaped annular wall is oriented outwardly relative to the longitudinal axis of the passage/chamber.

In one embodiment, the surface portion of the shaped annular wall is linear (such as for example a chamfered section) but could be non-linear or curvilinear. Other forms will be apparent to the skilled reader.

In another embodiment, a surface portion of the shaped annular wall is arranged so as to be operable with the fluid mixing assembly so that a region of space therebetween is variable.

In a further embodiment, positional adjustment of the fluid mixing assembly relative to the shaped annular wall serves to provide an annular nozzle operable for, at least in part, modifying or controlling one or more characteristics of the flow of fluid into and/or through the chamber.

In one embodiment, the surface portion (such as for example, the outward oriented surface portion) of the shaped annular wall is arranged operable with the periphery of the rotating member so that the region of space therebetween is variable. Arrangements of this nature therefore allow the volume and/or velocity of heated fluid passing the rotating member to be variable.

Variability of the region of space between the periphery of the rotating member and the shaped annular wall may be adjusted manually, or could be arranged so as to be adjusted automatically by an appropriate control system. Adjustment by such control system could be informed by one or more sensor units (such as for example flow and/or temperature measurement sensors) positioned throughout the chamber.

In one embodiment, the means for managing the thermal state of the heated fluid comprises one or more sensor units provided at locations along the flow of heated fluid. Such sensor units may, for example, include any one or more suitable temperature sensors, pressure sensors, and/or flow velocity sensors (which could be configured so as to measure the effective or average velocity of the flow, and/or the velocity of any localised eddy flows). It will be appreciated that other sensors may be used to measure other physical characteristics of the environment to determine its real-time thermal state. In this manner, the thermal state of the fluid flow can be monitored for control/management purposes in order to ensure that the risk of the mineralogy of the material to be dried becoming compromised is reduced or avoided for subsequent analysis purposes.

In one embodiment, the means for managing the thermal state of the fluid comprises one or more temperature sensors (such as for example, thermocouples) placed within the chamber at selected locations. In this manner, the temperature adjacent the location of the or each temperature sensor can be measured and used to inform any appropriate response. Any such response may be by way of seeking to facilitate a change to the thermal state within the chamber: either by way of, for example, increasing the temperature of the heated flow of fluid, or causing a decrease in the temperature of the heated fluid flow.

In one embodiment, the data measured by the one or more sensor units is observed or measured manually, and any response deployed/executed in a manual manner.

In another embodiment, the monitoring of the one or more temperature sensors is conducted so that the measured value is about the predetermined temperature level.

In a further embodiment, at substantially the commencement of a drying operation, one or more temperatures within the chamber is below about 90 degrees Celsius.

It will be appreciated that the management of the thermal state of the fluid flow could be executed in an autonomous manner. Thus, in one embodiment, the means for managing the thermal state of the heated fluid flow comprises a thermal management unit configured for controlling and/or managing the thermal state of the fluid within the chamber and/or conduit (that providing fluidic communication between the chamber and the collection means) so that drying of the moisture laden material occurs in a manner which serves to reduce or avoid the potential risk of compromising the mineralogy of the constituents of the material or sample being dried.

In one embodiment, the thermal state within the chamber can be monitored and/or controlled by the thermal management unit so as to substantially maintain, or seek to maintain, a desired thermal profile considered appropriate for drying the input material so as to avoid the potential risk of compromising the materials constituent mineralogy.

In some embodiments, the thermal management unit is operable for monitoring and/or controlling the thermal profile of the fluid along a portion of the flow path which, in one arrangement, extends from within the chamber to at or near the collection means.

In one embodiment, the thermal management unit is operable for monitoring and/or controlling the temperature of the fluid at one or more locations along a portion of the flow path.

In some embodiments, the thermal management unit is configured operable for varying the temperature of the fluid at one or more locations within the chamber in response to monitoring the thermal state (which may include the thermal profile or temperature profile) of the fluid along a portion of the flow path.

In one embodiment, the thermal management unit comprises a temperature controller. In one arrangement, the temperature controller is configured operable so as to be capable of varying the temperature of the output of the heat source. In one such arrangement, for example, the temperature controller is arranged operable for varying the voltage applied or supplied to an electrical heat source (eg. the heating element).

The thermal management unit may comprise one or sensors configured appropriate for sensing or measuring the temperature (eg. thermocouples) of the fluid.

The temperature profile of the heated fluid flow may comprise one or more temperature measurements taken at more than one locations along a portion of the flow path.

In one embodiment, a predetermined temperature profile of the heated fluid flow may be one in which temperature values at specific locations along the flow path are desirous or values known to correspond with a temperature profile providing an acceptable thermal environment for drying purposes.

The introduction of moisture laden sample material into the chamber serves to, at least in part, modify the thermal profile of the fluid in the chamber. In a general sense, the effect of introducing raw moisture laden material can be to reduce the effective temperature of the flowing fluid in the chamber. As the moisture laden sample of material begins to dry (and exit from the chamber when sufficiently dry), the thermal profile will change by way of the temperature of the fluid increasing. Thus, the rate at which the moisture laden material is introduced into the chamber (and dried material leaving the chamber) serves to, at least in part, alter the thermal state of the fluid in the chamber—which changes can be monitored by the thermal management unit.

In another embodiment, the thermal management unit can be arranged in operable association with the input means. In one arrangement, the monitoring of the thermal state of the fluid within the flow path may be used to control and/or manage the rate at which material to be dried is introduced into the chamber by way of the input means so that drying of the material occurs in a manner which serves to reduce or avoid the potential risk of compromising the mineralogy of the constituents of the material. Furthermore, the thermal management unit can be configured operable for seeking to maximise efficiency of the drying process and/or seek to prevent the apparatus from becoming overloaded.

One or more valve assemblies may be used to manage the pressure differential between the pressure in the chamber as compared to a predetermined reference pressure (such as for example, ambient conditions). Control of the pressure differential may have the effect of controlling flow velocities of the flow of heated fluid and could serve to slow the flow velocity along a section of the flow path of the heated fluid so as to allow the dried material to be cooled during carriage to the collection means. Thus, one or more valve assemblies could be employed along the path of the heated fluid flow so that the pressure differentials can be actively managed/controlled. Actuation of the or each valve assembly may be controlled manually, or could be automated by way of an appropriate control system, such as for example, by the thermal management means. While the necessity is largely driven by application, similar means may also be configured for controlling/managing cooling of the temperature of the fluid flow.

In some embodiments, the apparatus may comprise X-ray fluorescence (XRF) and X-ray diffraction (XRD) sensors (such as for example, laser-induced breakdown spectroscopy (LIBS) sensor units) for analysing material dried in the chamber. In one arrangement, such sensors may be incorporated or associated with the collection means, or could be provided as part of any transport arrangement used to carry dried material from the chamber. The skilled person would readily appreciate where such sensors could be provided for advantageous operation of the apparatus.

In another embodiment, any X-ray fluorescence (XRF) and X-ray diffraction (XRD) or like sensors for analysing material dried in the chamber are provided as external components to the apparatus.

In some embodiments, the apparatus may be arranged so as to be portable for use at different geographical locations. In this regard, the apparatus can be readily configurable so that one or more of its components (such as the chamber) can be readily mounted or supported temporarily. In one embodiment, the apparatus could be mounted to a frame, either in a permanent or temporary manner, the frame itself being arranged to be movable.

In some configurations, and without being bound by preliminary results, embodiments of the apparatus may be configured for drying approximately 100 g to 200 g of sample material in a time period of from about 2 minutes to about 5 minutes. In some test embodiments, a rate of drying sample material to an acceptable moisture content in the order of about 10 g per minute can be achieved.

In one embodiment, an amount of sample material of about 150 g can be dried in a time period of between about 2 minutes to 3 minutes, with below about 5 grams of material remaining in the chamber. In other test embodiments, a rate of drying material to a desired moisture content in the order of about 75 g of moisture laden material per minute can be achieved.

In some configurations, embodiments of the apparatus may be arranged to reduce the moisture content of a sample of material to below about 1 percent by weight.

In one embodiment, embodiments of the apparatus are part of a field portable system for on-site analysis of geological material.

Embodiments of the apparatus of the present principal aspect may be arranged or operably configured for use in drying and disaggregating, in a batch or continuous manner, a sample of geological material having a substantial moisture content.

According to a second principal aspect, there is provided a spin flash dryer comprising any embodiment of the apparatus of the first principal aspect.

Embodiments of the spin flash dryer of the present principal aspect may be arranged so as to comprise an apparatus for use in drying and disaggregating, in a batch or continuous manner, a sample of geological material having a substantial moisture content, the apparatus being arranged in accordance with any embodiment of the apparatus of the first principal aspect.

Thus, embodiments of the apparatus arranged in accordance with the first described principal aspect may be provided in the form of a spin flash drying apparatus configured for drying geological materials and which are not generally in a state to be analysed appropriately using XRF and XRD technologies. As part of lab-at-rig (LAR) arrangements, spin flash drying is envisaged as providing a potential solution to rapidly drying materials for allowing them to be analysed in near real-time by the XRF and XRD sensors which may be built into the system, as well as other relevant sensors.

According to a third principal aspect, there is provided a method for drying a sample of geological material having a substantial moisture content, the method comprising:
  providing a flow of heated fluid, and
  managing a thermal state of the flow of heated fluid so as to facilitate a reduction of the moisture content of a portion of the sample of material which becomes exposed to the flow of heated fluid while substantially preserving one or more chemical and/or physical properties of the portion.

It will be appreciated that the method of the present aspect may incorporate method steps which correspond to any of the features described above in relation to the apparatus of the first principal aspect or the spin flash dryer of the second principal aspect. Thus, features of the first and/or second principal aspects may be incorporated or adapted for use with the present method.

In one embodiment, the means for providing a flow of heated fluid and the means for managing the thermal state of the heated fluid flow are arranged operable for providing rapid or expeditious drying of the portion.

In one embodiment, the method comprises exposing the sample of geological material to the flow of heated fluid.

In one embodiment, the thermal state of the flow of heated fluid is managed in a manner so as to facilitate a reduction of the moisture content of the portion of the sample to substantially below a predetermined level while substantially preserving one or more chemical and/or physical properties of the portion.

In another embodiment, the managing of the thermal state of the heated fluid flow is performed so as to facilitate a substantial reduction of the moisture content of a portion of the sample while the temperature of the portion remains substantially below a predetermined temperature level. Optionally, the predetermined temperature level is about 105 degrees Celsius.

In one embodiment, managing the thermal state of the flow of heated fluid comprises modifying one or more characteristics of the fluid so as to facilitate a reduction of the moisture content of a portion of said sample to substantially below a predetermined level within a predetermined time period while substantially preserving one or more chemical and/or physical properties of said portion.

In one embodiment, providing a flow of heated fluid comprises heating a quantity of fluid by way of a fluid heating means. The heating means comprising, for example, a heat source such as a cartridge heater.

In one embodiment, the method includes facilitating or providing a low pressure region downstream of the fluid heating means so as to, at least in part, encourage or facilitate the flow of heated fluid.

In another embodiment, the method comprises introducing, directing, or injecting heated fluid in a manner causing to introduce a component of angular or rotational motion into the heated flow.

In a further embodiment, providing the flow of heated fluid involves introducing a rotational, non-linear, or unsteady component of flow into a flow of heated fluid.

In a further embodiment, the method comprises introducing, directing, or injecting heated fluid into a passage through which the heated fluid flows, the introducing, directing, or injecting of the heated fluid into the passage operable in a direction tangential to the passage. In such embodiments, the method comprises introducing, directing or injecting heated fluid in a manner causing engagement of the fluid with a fluid mixing assembly. In one embodiment, the fluid mixing assembly is arranged in accordance with the fluid mixing assembly described in relation to the first principal aspect.

In one embodiment, managing the thermal state of the flow of heated fluid comprises monitoring one or more physical characteristics of the fluid flow.

In another embodiment, managing the thermal state of the flow of heated fluid comprises monitoring the temperature, pressure, and/or flow velocity of the heated fluid at one or more locations along the path of the flow of the fluid. It will be appreciated that other physical parameters of the fluid flow may be monitored for management of the thermal state of the flow of heated fluid.

In one embodiment, managing the thermal state of the flow of heated fluid comprises determining whether the monitored temperature, pressure, and/or flow velocity of the heated fluid corresponds with an appropriate thermal profile considered acceptable for drying of the sample.

In another embodiment, managing the thermal state of the flow of heated fluid comprises adjusting the temperature, pressure, and/or flow velocity of the heated fluid at one or more locations along the path of flow of the fluid in response to monitoring the temperature, pressure, and/or flow velocity of the heated fluid at one or more locations along the path of flow of the fluid.

In one embodiment, the method may further comprise causing fluid heated by the fluid heating means to engage a rotating member of the fluid mixing assembly so as to promote, at least in part, rotational or unsteady fluid flow along a portion of the path of flow.

In one embodiment, managing the thermal state of the flow of heated fluid comprises adjusting the position of the fluid mixing assembly to adjust the velocity of the flow of heated fluid as might be required.

In another embodiment, the method includes causing or facilitating the modification of the sample material so as to increase its effective surface area, so providing for increased exposure of the sample of material, in its modified form, to the flow of heated fluid for drying purposes.

In another embodiment, the method comprises disaggregating the sample material by way of an appropriate disaggregating/comminution means, such means configured for engaging with the sample material for the purpose of modifying the sample for increasing the effective surface area of the sample material which is exposed to the heated fluid flow.

Modifying of the sample may be performed, in part, by exposing one or more portions of the sample to centripetal forces, such forces being imparted by way of the portions coming into contact with the rotating member and/or the fins or protrusions carried thereby. In some implementations, the centripetal forces serve to reintroduce the portions to the flow of heated fluid.

The method may comprise causing or facilitating repetitious exposure of portion(s) of the sample to the flow of heated fluid until sufficiently dry so as to be carried by the heated flow of fluid for collection purposes.

In one implementation, the method comprises modifying the thermal state and/or flow of heated fluid so as to expeditiously facilitate a substantial reduction of the moisture content of a portion of the sample while the temperature of the portion remains below a predetermined temperature level so as to substantially preserve one or more chemical and/or physical properties of said portion.

The method may further comprise transporting dried material to a collection means, such as for example, a collection receptacle. In one implementation, carriage of the dried material is, in part, assisted by the flow of heated fluid.

In one embodiment, collection of the dried material can be by way of cyclonic separation.

The method may further comprise separating portions of the dried material for subsequent processing/analysis purposes. In one embodiment, the method includes classifying the collected dried material into specific predetermined size ranges.

In one embodiment, the temperature of the heated flow of fluid is managed so as to be below about 105 degrees Celsius. In this manner, the temperature of the sample of material dried by way of the present method is below about 105 degrees Celsius. In some situations, lower temperatures might be preferable/suitable for achieving acceptable drying rates depending the circumstances to hand.

In another embodiment, the heated flow of fluid is managed so as to reduce the moisture content of the sample portion to below about 1 percent by weight.

In a further embodiment, operation of the method results in providing a disagglomerated or disaggregated free flowing powder.

In another embodiment, the method comprises drying the material in discrete batches.

In a further embodiment, operation of the method provides from about 100 grams to about 200 grams of dried material in a time period of from about 2 minutes to 5 minutes, or from about 2 minutes to about 3 minutes.

In another embodiment, the method is performed at a remote location.

Embodiments of the method of the third principal aspect may be implemented using any embodiment of an apparatus arranged in accordance with the apparatus of the first principal aspect described above, or any embodiment of a spin flash dryer arranged in accordance with the spin flash dryer of the second principal aspect described above.

Embodiments of the method of the present principal aspect may be arranged or operably configured for providing a method for drying and disaggregating, in a batch or continuous manner, a sample of geological material having a substantial moisture content.

According to a further principal aspect, there is provided a method for drying geological material, the method comprising performing any implementation of a method arranged in accordance with the method of the third principal aspect using any embodiment of an apparatus arranged in accordance with the apparatus of the first principal aspect, or using any embodiment of a spin flash dryer arranged in accordance with the spin flash dryer of the second principal aspect.

In one embodiment, the method of the present aspect is performed at a remote location.

In another embodiment, the method of the present aspect or the third principal aspect is part of an overarching method for the extraction and analysis of geological material.

Embodiments of the method of the present principal aspect may be arranged or operably configured for providing a method for drying and disaggregating, in a batch or continuous manner, a sample of geological material having a substantial moisture content.

According to a further principal aspect, there is provided a system for use in drying a sample of geological material having a substantial moisture content, the system comprising:

a means for providing a flow of heated fluid; and a means for managing a thermal state of the flow of heated fluid, said means arranged operable with the means for providing a flow of heated fluid so that exposure of the sample to the flow of heated fluid facilitates a reduction of the moisture content of a portion of the sample while substantially preserving one or more chemical and/or physical properties of the portion.

In one embodiment, the means for providing a flow of heated fluid and the means for managing the thermal state of the heated fluid flow are arranged operable for providing rapid or expeditious drying of the portion.

In one embodiment, the system comprises a means for exposing the sample of geological material to the flow of heated fluid.

In one embodiment, the means for managing the thermal state of the flow of heated fluid is configured operable for facilitating a reduction of the moisture content of the portion of the sample to substantially below a predetermined level while substantially preserving one or more chemical and/or physical properties of the portion.

In another embodiment, the means for managing the thermal state of the flow of heated fluid is configured operable for facilitating a substantial reduction of the moisture content of a portion of the sample while the temperature of the portion remains substantially below a predetermined temperature level. Optionally, the predetermined temperature level is below or about 105 degrees Celsius.

In one embodiment, the means for managing the thermal state of the flow of heated fluid is configured operable for modifying one or more characteristics of the fluid so as to facilitate a reduction of the moisture content of a portion of said sample to substantially below a predetermined level within a predetermined time period while substantially preserving one or more chemical and/or physical properties of said portion.

In one embodiment, the means for providing a flow of heated fluid comprises heating a quantity of fluid by way of a fluid heating means.

In one embodiment, the means for providing a flow of heated fluid includes facilitating or providing a low pressure region downstream of the fluid heating means so as to, at least in part, encourage or facilitate the flow of heated fluid.

In another embodiment, the means for providing a flow of heated fluid comprises a means for introducing, directing, or injecting heated fluid in a manner causing to introduce a component of angular or rotational motion into the heated flow. In this manner, a rotational, non-linear, or unsteady component of motion may be introduced into the heated fluid flow.

In one embodiment, the means for managing the thermal state of the flow of heated fluid comprises monitoring one or more physical characteristics of the fluid flow such as, for example, the temperature, pressure, and/or flow velocity of the heated fluid at one or more locations along a flow path of the heated fluid.

In another embodiment, the means for managing the thermal state of the flow of heated fluid is configured operable for adjusting the temperature, pressure, and/or flow velocity of the heated fluid at one or more locations along the path of flow of the fluid in response to monitoring the temperature, pressure, and/or flow velocity of the heated fluid at one or more locations along the path of flow of the fluid.

In another embodiment, the system comprises a means for causing or facilitating a modification of the sample material so as to increase its effective surface area, so providing for increased exposure of the sample of material, in its modified form, to the flow of heated fluid for drying purposes.

In one embodiment, the system comprises a means for collecting dried sample material.

In one embodiment, the system comprises a means for separating portions of the dried material for subsequent processing/analysis purposes.

It will be appreciated that embodiments of the system of the present aspect may incorporate features which correspond to any of the features described above in relation to the apparatus of the first principal aspect, the spin flash dryer of the second principal aspect, or the methods of the above described principal aspects. Thus, features of the principal aspects described herein may be incorporated or adapted for use with the system of the present aspect. Furthermore, embodiments of the present system may be configured operable for performing any of the methods for drying a sample of geological material as described herein.

According to a further principal aspect, there is provided a method for drying a sample of geological material having a substantial moisture content using any embodiment of a system arranged in accordance with the system of the previous principal aspect.

The principal aspects described herein can be practiced alone or in combination with one or more of the other principal aspects, as will be readily appreciated by those skilled in the relevant art. The various principal aspects can optionally be provided in combination with one or more of the optional features described in relation to the other principal aspects. Furthermore, optional features described in relation to one example (or embodiment) can optionally be combined alone or together with other features in different examples or embodiments.

For the purposes of summarising the principal aspects, certain aspects, advantages and novel features have been described herein above. It is to be understood, however, that not necessarily all such advantages may be achieved in accordance with any particular embodiment or carried out in a manner that achieves or optimises one advantage or group of advantages as taught herein without necessarily achieving other advantages as may be taught or suggested herein.

It is to be noted that principles of the present invention are not to be limited in scope by any of the specific embodiments described herein. These embodiments are intended for the purpose of exemplification only. Functionally equivalent products, formulations and methods are clearly within the scope of the invention as described herein.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

In the figures, like elements are referred to by like numerals throughout the views provided. The skilled reader will appreciate that elements in the figures are illustrated for simplicity and clarity and have not necessarily been drawn to scale. For example, the dimensions and/or relative positioning of some of the elements in the figures may be exaggerated relative to other elements to facilitate an understanding of the various embodiments described herein. Also, common but well understood elements that are useful or necessary in a commercially feasible embodiment are often not depicted in order to provide a less obstructed view of these various embodiments. It will also be understood that the terms and expressions used herein adopt the ordinary meaning as is accorded to such terms and expressions with respect to their corresponding respective areas of inquiry and study except where specific meanings have otherwise been set forth herein.

Specifically, reference to positional descriptions, such as 'lower' and 'upper', and associated forms such as 'uppermost' and 'lowermost', are to be taken in context of the embodiments shown in the figures, and are not to be taken as limiting the principles of the invention to the literal interpretation of the term, but rather as would be understood by the skilled reader. Furthermore, reference to positional descriptions, such as 'upstream' and 'downstream', are to be taken in context of the embodiments shown in the figures, and are not to be taken as limiting the invention to the literal interpretation of the term, but rather as would be understood by the skilled reader.

DESCRIPTION OF EMBODIMENTS

Embodiments described herein may include one or more range of values (eg. size, displacement and field strength etc). A range of values will be understood to include all values within the range, including the values defining the range, and values adjacent to the range which lead to the same or substantially the same outcome as the values immediately adjacent to that value which defines the boundary to the range.

Other definitions for selected terms used herein may be found within the detailed description and apply throughout. Unless otherwise defined, all other scientific and technical terms used herein have the same meaning as commonly understood to one of ordinary skill in the art to which the invention belongs.

Figure 1:
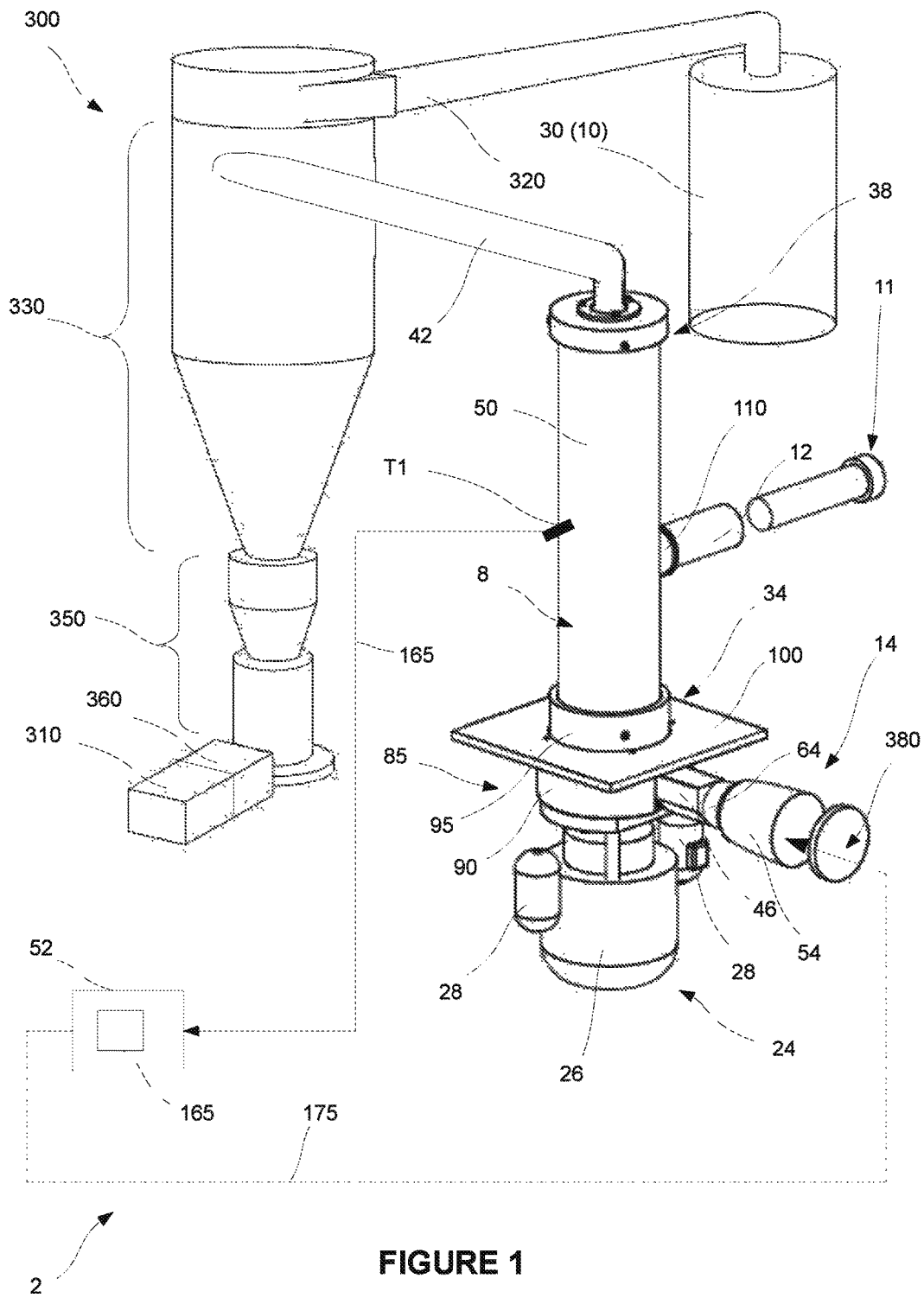
FIG. 1 shows a schematic perspective of one embodiment arranged in accordance with the principles of the invention.
Figure 2:
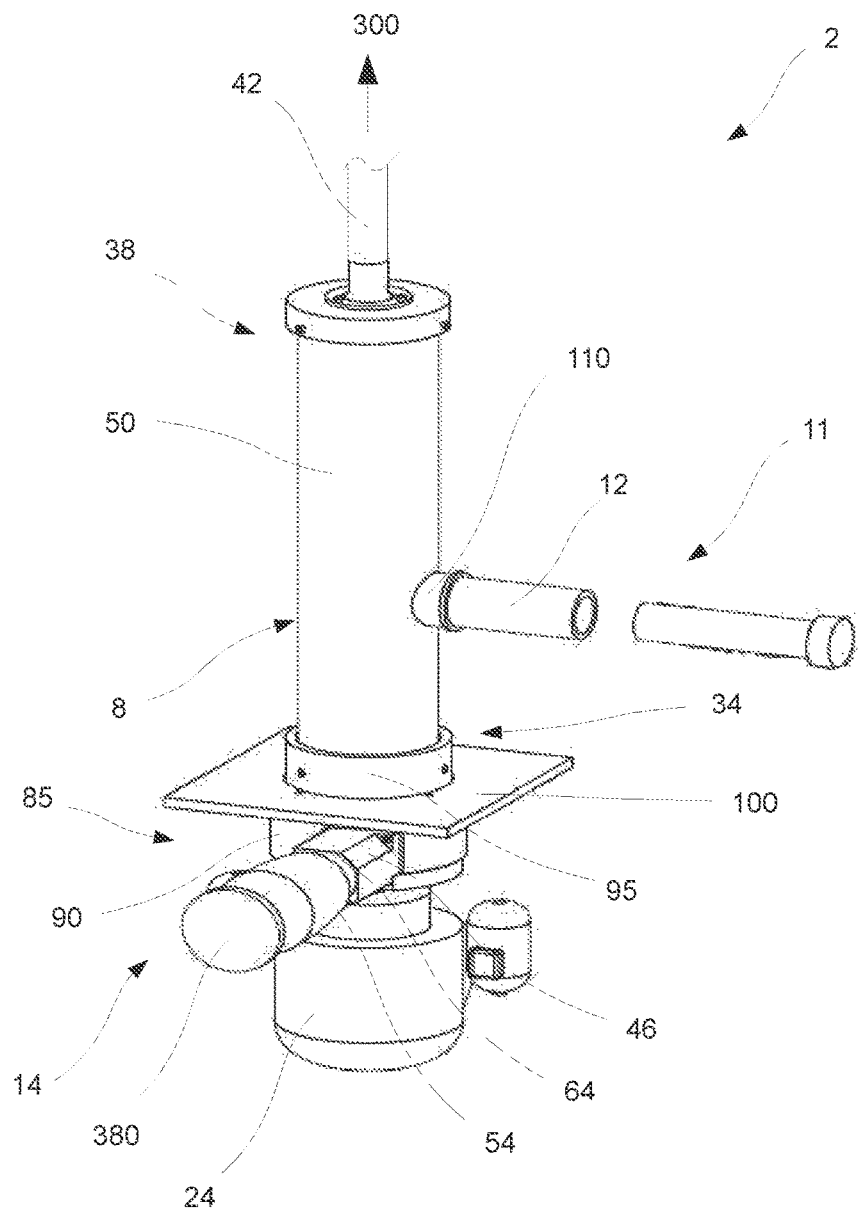
FIG. 2 shows a schematic perspective view of the chamber of the embodiment shown in FIG. 1.

FIG. 1 shows schematic perspective view of one embodiment of an apparatus 2 used for drying generally moisture laden (typically in the order of about 30% moisture content) geological material samples as extracted in a natural or 'raw' state (often a fine granular sticky clay/mud) from a remote geological drilling site, the drying being performed in a manner which seeks to preserve the minerology of the material sample. The apparatus 2 comprises a chamber 8 which defines a passage into which a sample of geological material to be dried is introduced by way of a feed assembly 11 which is associated with the chamber 8 as shown.

The apparatus 2 includes a means for providing a heated fluid flow. In this regard, the apparatus 2 includes a fluid distribution assembly 10 configured operable with a heat source 14 (provided in the form of an in-line heating element 54 operably associated with a temperature controller 155) for providing the heated airflow. The fluid distribution assembly 10 comprises a vacuum means configured so as to facilitate a flow of fluid within the passage defined by the chamber 8. In the embodiment shown in the Figures and described herein, the vacuum means is provided in the form of vacuum unit 30 (in at least one prototype embodiment, the vacuum means was provided in the form of a Sonixx 2400 W (bagless) cyclonic vacuum unit). The fluid distribution assembly 10 further comprises a fluid mixing assembly 16 provided in the form of a rotating member such as an impeller 20 driven by an electric motor 24. The fluid mixing assembly 16 is configured operable for, at least in part, introducing a rotational component of motion into the heated fluid flow. The impeller 20 is provided at a first end 34 of chamber 8, and arranged so that its axis of rotation is substantially aligned with a longitudinal axis X of the chamber. Thus, in the form shown in the figures, impeller 20 is arranged concentric with chamber 8.

The apparatus 2 further comprises a means 52 for managing the thermal state of the heated fluid flow which is arranged operable with the fluid distribution assembly 10 for drying the moisture laden material so that exposure of the sample material to the heated air flow facilitates a reduction of the moisture content of a portion of the sample while seeking to preserve one or more chemical and/or physical properties of the portion (ie. seeking to substantially preserve the mineralogy of the sample portion). In this manner, any prospective risk in compromising the integrity of the resulting dried material for subsequent analysis processes is avoided or, at the least, reduced. Operation of the apparatus 2 generally seeks to provide a disagglomerated or disaggregated free flowing powder appropriate for analysis/processing purposes.

The apparatus 2 also includes a means of disaggregating the input sample material for breaking the sample up into smaller portions (as outlined further below) thereby increasing the effective surface area of the sample for drying purposes. In the embodiment described and shown herein, the impeller 20 (and its fins/protrusions (74)) of the fluid mixing assembly 16 also serves to provide this disaggregation function. It will be appreciated that the disaggregation means may also be configured so as to provide a comminution function if needed. Thus, in this arrangement, the fluid mixing assembly 16 and the means for disaggregation (and/or comminution) of the sample material is provided by the same component (ie. impeller 20 with protrusions 74). In the embodiment shown, the impeller 20 is operable for rotating at a rate between about 15,000 to about 25,000 revolutions per minute, the rate of rotation being operable for at least: (1) promoting or facilitating, at least in part, rotational, non-linear, or unsteady flow of the fluid as it progresses downstream within the chamber 8; and/or (2) engaging with the sample material to be dried for the purpose of modifying the sample for increasing its effective surface area which is exposed to the heated fluid flow. The impeller 20 may be of stainless steel material but could be made from other suitable materials depending on the specific circumstances. It will be readily appreciated that the functions of facilitating the rotational nature of the heated flow, and disaggregation of the sample material could be performed by separate components.

The apparatus 2 also includes a collection means 300 arranged in fluid communication with the chamber 8 and configured operable for the collection of dried material in an appropriate collection receptacle 310. In the embodiment described herein, the collection means 300 is operably associated with the vacuum unit 30 by way of conduit 320. In this manner, the arrangement is configured such that the vacuum unit 30 facilitates flow of the heated fluid (and the dried sample material) to the collection means 300 where it is ultimately separated (by cyclonic separation).

As is shown throughout FIGS. 1 to 10, the chamber 8 is provided in cylindrical form (provided in the form of a finite length tube section) having opposite first 34 (upstream) and second 38 (downstream) ends. The first end 34 of the chamber 8 is arranged to locate and house the fluid mixing assembly 16 of the fluid distribution assembly 10. In use, the fluid distribution assembly 10 serves to provide a heated flow of fluid through the chamber 8 in the direction of the second (downstream) end 38. In the embodiment shown, the chamber 8 is provided having a volumetric capacity in the order of about 4,000 cubic centimeters. A volumetric capacity of this order has proven to provide good utility in allowing relatively small amounts of sample material to be dried in the desired manner while maintaining sample integrity, and allowing for portability of the apparatus 2. In this regard, the volumetric capacity of the chamber 8 is configured of a size appropriate for the quantity of the sample material input into the chamber to assist in the management of the thermal state of the flow of heated fluid for drying purposes. The performance of prototype embodiments suggest that the volumetric capacity of the chamber assists, at least in part, in providing a thermal environment which can be managed in order to reduce or avoid the risk of compromising the integrity of the mineralogy of the constituents of the sample when seeking to reduce the drying time. In this regard, the volumetric capacity of the chamber 8 may be configured of a size appropriate for a quantity of the sample material input into the chamber for drying the input sample material for achieving an acceptable level of moisture content in the dried sample material (in the order of below about 1% by weight) within an acceptable period of time (which can be between 2 minutes to 5 minutes).

The second end 38 of the chamber 8 is arranged so as to be in fluid communication with the vacuum unit 30 by way of conduits 42, 320 configured as shown in FIG. 1. When in use, the vacuum unit 30 serves to, at least in part, assist in encouraging the collection of dried material leaving the chamber 8 (by way of being carried by the fluid flow) in the collection receptacle 310 via the cyclone unit 330. In the embodiment shown, conduit 42 is provided in the form of a hose or tube section which is connected to the second end 38 of the chamber 8 in a substantially concentric manner (relative to the orientation of the longitudinal axis X of the chamber). Similarly, conduit 320 is also provided in the form a hose or tube section arranged between the collection means 300 and the vacuum unit 30. Collection of the dried sample material is by way of cyclonic separation in which the dried material collects within the collection receptacle 310 by passing through the cyclone unit 330 fitted to vortex breaker unit 350. After collection of the dried sample, the dried sample material is transferred/removed through the use of a knife-gate valve 360. The knife-gate valve 360 also serves to provide an airtight seal for the collection receptacle 310 necessary for the function of the cyclone unit 330. In other arrangements, the collection receptacle 310 may be more directly associated (ie. arranged integral) with the vacuum unit 30.

Thus, the embodiment shown in FIG. 1 employs vacuum unit 30 for establishing the vacuum for creating the inherent flow of fluid through the chamber 8 to the collection means 300. The pressure differential provided by vacuum unit 30 assists with the development of the movement of fluid through the system, while the impeller 20 arrangement serves to encourage or help facilitate the rotational nature of the path of the heated airflow within the chamber 8. The presence of the pressure differential caused by the vacuum unit 30 assists in the carriage and collection of the dried material from the chamber 8 to the collection means 300.

The desired thermal state of the heated fluid flow may be defined by a thermal profile which is composed of information corresponding to any number of physical characteristic(s)/parameter(s) of the heated fluid flow, such as for example, temperature, pressure, and/or flow velocities at regions of interest along the fluid's flow path.

The means 52 for managing the thermal state of the heated fluid flow comprises one or more sensor units provided at locations along the flow of the heated fluid in the chamber 8 and/or conduit 42. Such sensor units may, for example, include any one or more suitable temperature sensors, pressure sensors, and/or flow velocity sensors (which could be configured so as to measure the effective or average velocity of the flow, and/or the velocity of any localised eddy flows). It will be appreciated that other sensors may be used to measure other physical characteristics of the environment to determine its real-time thermal state. In this manner, the thermal state of the fluid flow can be monitored for control/management purposes in order to ensure that the mineralogy of the sample material being dried is not compromised for analysis purposes.

For the embodiment shown in FIG. 1, a temperature sensor provided in the form a thermocouple T1 is provided within the chamber 8 (at the mid-section region of the chamber) and the output data (ie. temperature data) measured/monitored by an operator/user of the apparatus 2. In this manner, while the apparatus 2 is in use, an operator/user observes (165) the data received from the temperature sensor T1 to ensure that the sensed value(s) reflects an acceptable thermal state of the fluid flow for drying purposes. If needed, the operator/user may make an appropriate adjustment (175) so as to alter the thermal state of the heated fluid flow as required. Any such adjustment is made by way of adjusting the operational condition of the in-line heating element 54 by way of its associated temperature controller (155), which could be by increasing the output temperature and/or adjusting the flow velocity of any operable fan unit which might be used to assist movement of the air heated by the in-line heating element 54 (or, for example, adjustment to vacuum unit 30).

It will be understood that multiple temperature sensors could be monitored by the operator/user. For example, with regard to the arrangement shown in FIG. 11, three thermocouples (T1, T2, and T3) are provided and arranged to measure the temperature at selected locations within the chamber 8: at the lower region, mid-region, and upper-regions of the chamber 8. In at least one prototype embodiment, three temperature sensors were installed at regions: immediately upstream of the impeller 20, at the exit of the chamber 8, and further downstream within conduit 42, each recording about 200° C., 100° C., and 80° C. respectively. It will be appreciated that other measurement sensors could be employed and used to inform a control system (or operator/user) configured to manage the thermal state of the fluid flowing through chamber 8 and/or conduit 42.

Without being bound by results obtained by testing using preliminary prototype embodiments, the temperature sensor(s) may be monitored (manually or otherwise) to ensure that the temperature of the heated fluid in the chamber 8 remains substantially within the range of between about 90 to about 105 degrees Celsius during operation. It has been observed that favourable drying results occur when the temperature within the chamber 8 remains about 90 degrees Celsius. It will be appreciated that temperature variations are likely to occur during operation; for example, the temperature of the environment is likely to fall as moist sample material is introduced into the chamber 8, and will recover (or rise) as the input material begins to dry. In some situations, lower temperatures might be preferable/suitable for achieving acceptable drying rates and resulting form (of the dried material, eg. disaggregated or disagglomerated free flowing powder) depending the circumstances to hand.

It will be appreciated that as the level of sophistication of the monitoring/control of the thermal environment increases, the management of the thermal state of the fluid flow could be executed in a substantially autonomous manner. In such an embodiment, the means 52 for managing the thermal state of the heated fluid flow may comprise a thermal management unit 150 (see FIG. 11) arranged for monitoring and/or controlling the thermal state of the fluid within the chamber and/or conduit 42 so that drying of the material occurs in a manner which serves to reduce or avoid the potential risk of compromising the mineralogy of the constituents of the input material to be dried.

The thermal management unit 150 may be configured operable for monitoring (180), controlling (185), and/or managing a desirous thermal profile of the heated fluid as it moves along a portion of the flow path from within the chamber 8 to at or near its downstream end where the dried material is collected in the collection receptacle 310. In one embodiment shown in FIG. 11, the thermal management unit 150 is arranged operable for monitoring the temperature of the heated fluid flow at three locations along the flow path within the chamber 8 so that the thermal state of the fluid flow can be managed appropriately.

The thermal management unit 150 may be configured operable for varying the temperature of the fluid at one or more locations within the chamber 8 in response to monitoring the thermal state or thermal profile of the fluid within the chamber 8. In this manner, the thermal management unit 150 may further comprise temperature controller 155 which is configured operable so as to be capable of varying (185) the output of the heat source 14 (in-line heating element 54). In one arrangement, the temperature controller 155 may be arranged operable for varying the voltage applied or supplied to the electrical heat source 14 (or operation of the in-line heating element 54). It will also be appreciated that the axial position of the impeller 20 can be controlled (adjusted as discussed below) by way of the thermal management unit 150.

The thermal management unit 150 may also include one or more sensors units placed at locations along the fluid flow path that measure other physical parameters or characteristics of the flow which can be used to assist in managing the thermal environment within chamber 8. Effective/localised pressure and effective/localised flow velocities are examples of additional parameters which could be measured and used to inform any response needed to ensure the conditions remain appropriate for drying the material without risk to the constituent mineralogy of the sample material. Such parameters, along with temperature data, may all assist in informing the thermal management unit 150 of the estimated thermal profile (or thermal state) of the flow of heated fluid so that any response can be implemented if needed. The skilled reader will appreciate that other parameters could also be monitored.

Figure 11:
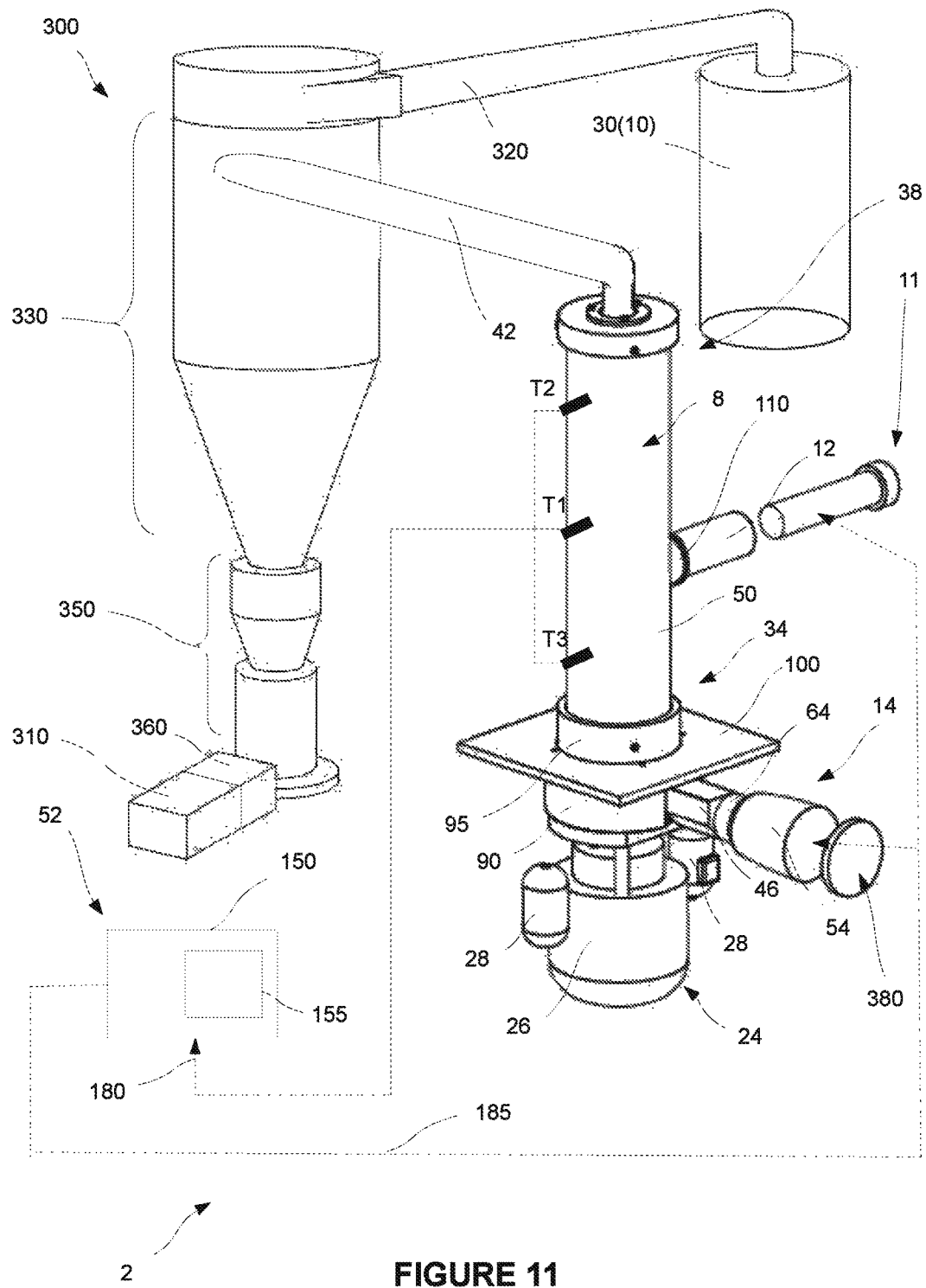
FIG. 11 shows a schematic perspective view according to another embodiment arranged in accordance with the principles on the invention.

With reference again to the arrangement shown in FIG. 11, the thermal management unit 150 may be arranged so as to control or inform the rate of introduction of sample material into the system for drying. As foreshadowed previously, it will be appreciated that the quantity and moisture content of the sample material introduced into the chamber 8 will have the effect of modifying the thermal profile of the fluid in the chamber. In a general sense, the effect in this instance is to reduce the net temperature of the fluid in the chamber 8. As the moisture laden sample material begins to dry and exit from the chamber 8, the thermal profile will change by way of the temperature of the fluid increasing. Thus, the rate at which the moisture laden material is introduced into the chamber 8 serves to, at least in part, alter the temperature profile of the fluid in the chamber—which changes can be monitored by the thermal management unit 150.

Embodiments of the apparatus 2 could be realised where the moisture content of the incoming material to be dried is measured and sent to the thermal management unit 52 for use in determining whether the thermal state of the heated flow of fluid requires adjustment. Any such adjustment can then be implemented at the appropriate time so that the thermal environment within the chamber 8 is maintained for appropriate operation.

As noted above, control or operation of the thermal management unit 150 may be conducted a number of ways. Monitoring and control of the thermal state of the heated fluid may be carried out manually by way of manual observation and selective adjustment of the necessary parameters as appropriate. However, as noted, the thermal management unit 150 may be configured so as to manage the thermal environment automatically. For example, in cases where the thermal environment is managed automatically, operation of the thermal management unit 150 could be by way of a programmed PCB or computer CPU. User interaction with the latter could be readily achieved by conventional means (ie. direct access with the programmable PCB or computer terminal) or by way of remote access via the internet using, for example, portable hand held devices such as smart phones, tablet computers and the like (which might include any known wireless protocols for connectivity purposes).

As noted above, the apparatus 2 includes an integrated separation assembly 360 arranged in operable association with the collection means 300 so that dried material can be separated or classified into specific predetermined portions or sizes of material. The collection receptacle 310 can be configured so as to be emptied (for example, automatically or by manual means) at defined or predetermined intervals. In some arrangements, the defined or predetermined intervals can be prescribed by a user. Emptying of the collection receptacle 310 is, for example, for the purposes of analysis and/or archiving. Means for sample splitting (for example, for providing analytical sampling and/or for archiving purposes) can be achieved by use of a cone splitter or tiered riffle splitter, or by other suitable means known to the skilled reader.

With regard to FIGS. 3 to 6, the heat source 14 fluidly connects with chamber 8 by way of a connecting means such as a manifold 46 attached to a mounting assembly 85 (described below). In the embodiment shown, the heat source 14 is provided in the form of the in-line heating element 54 which, when operable, serves to heat a body of fluid for introduction into the chamber 8.

The fluid distribution assembly 10 may include a means by which fluid heated by the heat source 14 may be directed, so that it may engage with the fluid mixing assembly 16. To this end, the in-line heating element 54 could be arranged operable with a fan unit to assist in fluid heated by the in-line heating element 54 being directed or blown into the chamber 8 as appropriate.

The manifold 46 is configured so as to ensure that substantially all air heated by way of the in-line heating element 54 is introduced or injected tangentially into chamber 8. As discussed above, the use of a fan unit with the heat source 14 is not generally required when a vacuum source such as vacuum unit 30 is fluidically connected to the chamber 8 for facilitating fluid movement therethrough. Furthermore, air for heating and introduction into the chamber 8 is preferably processed by way of a filtering means 380 so that air to be heated is appropriately filtered before entering the chamber 8.

The manifold 46 comprises a conduit portion 60 (see FIG. 5) which attaches to mounting assembly 85, the arrangement configured so as to provide a passage through which heated fluid (heated by way of the in-line heating element 54) can be introduced or injected into the chamber 8. Conduit portion 60 is dimensioned sufficiently so as to accommodate, in a substantially concentric manner about its longitudinal axis A, an outlet region 64 of in-line heating element 54. The skilled reader will appreciate that, in its simplest form, the relative dimensioning and/or fitting of conduit portion 60 and outlet region 64 is appropriate so as to ensure minimal leakage of heated air when introduced into the chamber 8. Manifold 46 is attached to a region of the mounting assembly 85 by bolts 87 (see FIG. 4), however, it will be appreciated that many other types of fastening arrangements could be used.

In the form shown in the Figures, manifold 46 is positioned upstream of impeller 20. In this arrangement, heated air from the in-line heating element 54 (temperatures of about 200 degrees Celsius were recorded immediately upstream of the impeller 20 in at least one prototype embodiment) is introduced from an upstream side of impeller 20. Furthermore, and with particular reference to FIG. 5, FIG. 6, and FIG. 8, the attachment of manifold 46 to the mounting assembly 85 is arranged so that the passage it provides for the conveyance of the heated fluid is offset from the longitudinal axis X of the chamber 8 by an offset distance 'd' (see FIG. 8). In this manner, heated fluid is introduced into chamber 8 in a substantially tangential manner (in a plane substantially transverse to the longitudinal axis X of the chamber 8). The effect of this is to facilitate appropriate mixing/movement of the heated air within the chamber 8 by, at least in part, imparting a component of angular or rotational motion to the heated fluid flow.

It will therefore be appreciated that the tangential introduction/injection of the heated air serves to assist in inducing a component of rotational motion to the fluid flow as it enters chamber 8. This can be encouraged by the flow of fluid moving substantially adjacent or across the internal wall of chamber 8, so imparting an angular or rotational component of motion into the flow of fluid. This rotational flow is then engaged by the impeller 20 where protrusions 74 act upon the fluid to further encourage and/or promote the generally rotational or unsteady flow through the chamber 8 (as it progresses downstream). The presence of a rotational flow has been found to be advantageous in ensuring sufficient exposure of the sample material introduced into the chamber 8 to the heated stream of air.

Figure 3:
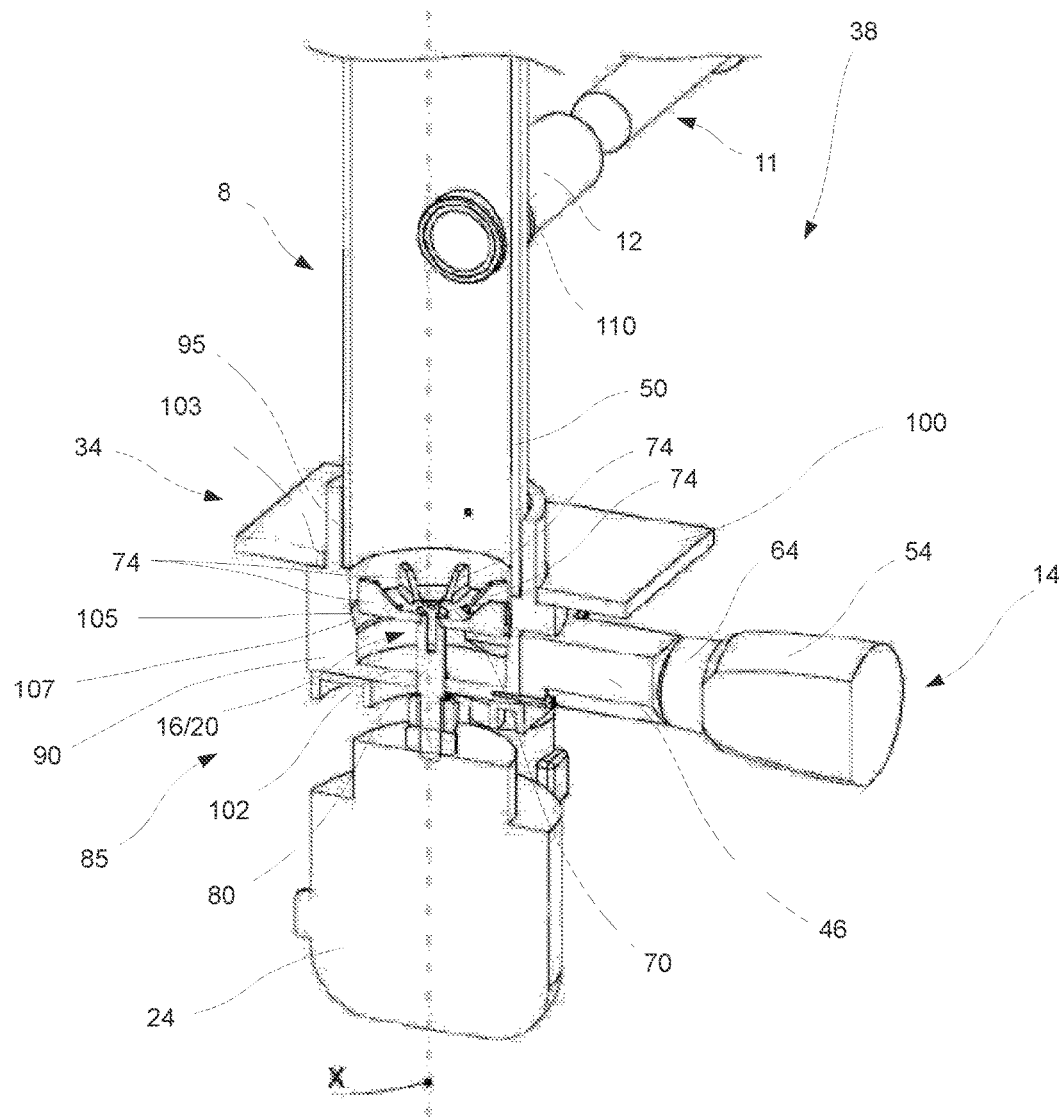
FIG. 3 shows a close up perspective view of a lower region of the chamber of the embodiment shown in FIG. 1 and FIG. 2, sectioned along the longitudinal axis X of the chamber.

As shown in at least FIG. 3, impeller 20 comprises a base 70 with a plurality of protrusions 74 extending outward from the base in a substantially downstream oriented direction. The protrusions 74 are shaped so as to promote fluid mixing/movement when the impeller 20 rotates and the protrusions engage with the heated fluid. The skilled person will appreciate that one or more of the protrusions 74 could be shaped so as to increase or reduce mixing or engagement with the heated fluid as desired. Protrusions 74 are provided in the form of elongate truncated fins, each regularly spaced about the base 70 and aligned radially from the centre region of the impeller 20.

Electric motor 24 drives impeller 20 by way of a drive coupling 80, which is configured sufficiently to provide enough space upstream of impeller 20 to allow for incoming heated fluid through manifold 46 (from the in-line heating element 54) from upstream (or below) the impeller 20. It would be appreciated that many different arrangements could be realised for providing an appropriate driving engagement between impeller 20 and motor 24 (which could be direct or indirect in nature). In the embodiment shown, the motor 24 is provided in the form of a router unit 26 (in this instance, a RT 1350 E plunge router from AEG) having handles 28.

With reference to FIG. 3, the cylindrical section defining the chamber 8 (and the chamber wall 50) is supported by the mounting assembly 85. The mounting assembly 85 comprises a body 90 having an annular flange 95, the flange being dimensioned sufficiently so as to receive end 34 of the chamber 8 therein. A plate 100 is provided about the annular flange 95 and arranged to bear against lip 103 (see FIG. 3) provided in the body 90. The plate 100 is fastened to body 90 by way of mechanical fastening system using a simple nut/bolt arrangement, however, it will be appreciated that any appropriate fastening system known in the art could be employed for this purpose.

The skilled reader will understand that plate 100 could readily be arranged to be removeably attachable to the body 90 so that the assembly of the chamber 8, mounting assembly 85, and electric motor 24 can be mounted or fastened to a supporting structure as desired, either in a permanent or removable manner. In such arrangements, such assembly could be connected to any desired mounting structure by way of for example plate 100 (ie. plate 100 supporting body 90). In this sense, apparatus 2 is arranged to be portable for use between different geographical locations.

A recessed region 102 is provided in the body 90 and defined in part by a shaped annular wall 105. With reference to FIG. 3, a portion of the shaped annular wall 105 is provided in the form of a chamfer which serves to define an outwardly (relative to the longitudinal axis X of the chamber 8) oriented linearly sloping surface portion 107 (hereinafter, 'chamfered' section).

The chamfered section 107 of the shaped annular wall 105 is operable with the impeller 20 of the fluid mixing assembly 16 so that the clearance available between the periphery of the impeller 20 and the shaped annular wall 105 may be varied. In this manner, the impeller 20 is arranged to be moveable or translatable in the direction of the longitudinal axis X, so allowing the clearance with the shaped annular wall 105 to be adjustable. This therefore allows the volume and/or velocity of heated fluid passing by the impeller 20 to be varied, and therefore controlled depending on the volume of heated fluid required/desired in order to maintain sufficient flow velocities and/or internal fluid flow stream temperatures in the chamber 8. It will be appreciated that operation of the apparatus 2 can be optimised if needed given that the air flow and the impeller 20 position can be independently variable.

Thus, positional adjustment of the impeller 20 in the axial direction of the chamber 8 (or height control in the vertical oriented arrangement shown) in association with the shaped annular wall 105 assists in controlling the volume and velocity of heated air available for engaging the impeller 20 following introduction (tangentially) by way of the in-line heating element 54. In this manner, operable association between the impeller 20 and the shaped annular wall 105 by way of positional adjustment serves to provide an upstream annular nozzle arrangement assisting in developing the generally rotational flow of heated fluid through the chamber 8.

For practical purposes, the flow of air through manifold 46 may be reversed. Reversing the flow of air through the manifold 46 by use of, for example, a "T" or appropriate valve can serve to evacuate chamber 8 and/or the region upstream of the chamber (that adjacent to the impeller 20) of any material that fails to be transferred out of the drying chamber. This is necessary to provide for sample cleaning to maintain sample integrity, minimise carryover, and therefore reduce the risk of contamination of subsequent samples. Additionally, positional adjustment of the impeller 20 can assist for cleaning purposes when seeking to remove any contaminants from the base (eg. recessed region 102) of the chamber 8 and/or the manifold 46.

Active control/adjustment of the height of the impeller 20 can assist in altering the operational characteristics of the apparatus 2 in real-time if required. In this manner, the thermal state of the heated fluid flow could be controlled as required in order to maintain an acceptable thermal state. The skilled reader will appreciate that technology providing for the automation of the positional adjustment of the impeller 20 could be readily employed to seek to optimise the desired flow characteristics for any material sample type. Furthermore, manual/automated adjustment of the impeller 20 in combination with the shape of the annular wall 105 could realise many different configurations which could serve to advantageously manipulate the flow characteristics of the incoming heated fluid in order to optimise the performance of the apparatus 2. For example, rather than the chamfered section 107 being linear, this section of the shaped annular wall 105 could be curvilinear in nature. Alternatively, the position of the impeller 20 could remain constant and the shape of the annular wall 105 could be arranged to be adjustable. In the embodiment shown in FIG. 11, operational control of the position of the impeller 20 is managed by the thermal management unit 52.

It will be appreciated that a range of sensors could be used to measure a variety of performance characteristics, the or each sensor being monitored and used to cause or facilitate specific adjustments to ensure the apparatus operates as might be required for drying a specific geological material of interest. For example, temperature and air flow sensors could be provided at various locations throughout the chamber 8, and used to inform the degree of adjustment needed to be made to the position of the impeller 20 to favour a desired operating objective, ie. substantially constant internal operating temperature (for a given geological sample, for example), and/or a predetermined fluid flow velocity at any specific location within the chamber 8.

The apparatus 2 may comprise or be configured operable with X-ray fluorescence (XRF) and X-ray diffraction (XRD) sensors for analysing dried material. Such sensors may be incorporated within the collection receptacle 310, or could be provided as part of any transport arrangement used to carry dried material from the chamber 8. The skilled person would readily appreciate where such sensors could be provided for advantageous operation.

The chamber 8 is formed from a material having favourable heat capacity or thermal capacitance characteristics so as to exploit the presence of a thermal mass and minimise temperature variations. In the embodiment shown, the material of chamber 8 is steel having a relatively high heat capacity or thermal capacitance. Thus, moisture variations occurring within the chamber 8 (or at various locations in the flow stream) during operation can be dampened or compensated for relatively quickly and are therefore less likely to compromise the thermal environment within the chamber 8. Similar may also apply to the material from which conduit 42 is provided of.

In some situations, it may also be advantageous to employ materials having good insulation properties or high thermal conductivity. In this manner, such materials may serve to provide improved cooling capability so as to prevent, at least in part, 'caking' of the input material on the chamber interior walls. Furthermore, it may also be necessary to line the interior wall of the chamber 8 with a non-stick, thermally stable material such as for example, polytetrafluoroethylene (Teflon), to reduce material retention in the chamber and maintain sample integrity.

Figure 4:
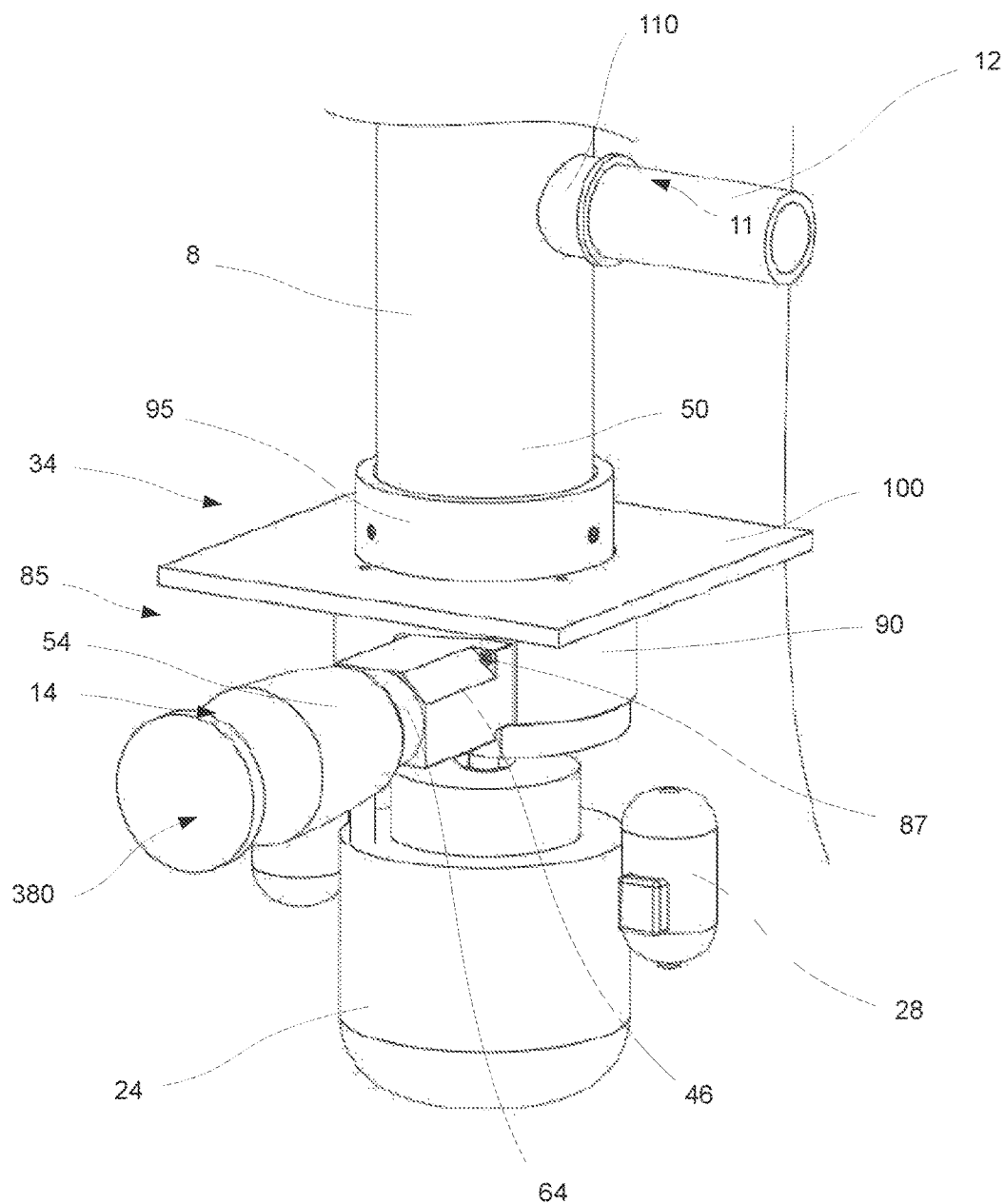
FIG. 4 shows another close up perspective view of a lower region of the embodiment shown in FIG. 1 and FIG. 2.
Figure 5:
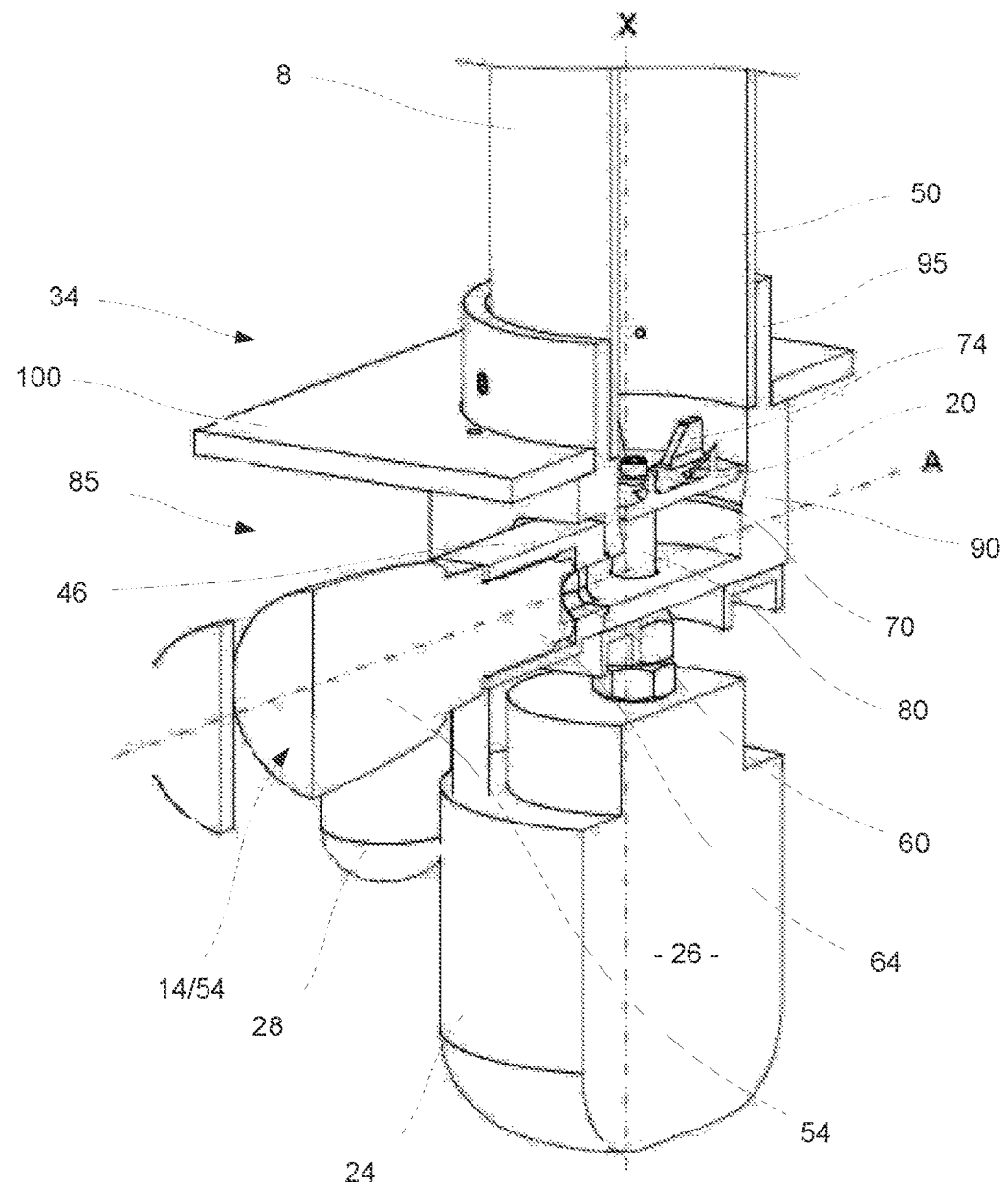
FIG. 5 shows a further close up perspective view of a lower region of the chamber of the embodiment shown in FIG. 1 and FIG. 2, sectioned along a plane (a vertical oriented plane in view of the embodiment shown) running through the longitudinal axis A.
Figure 6:
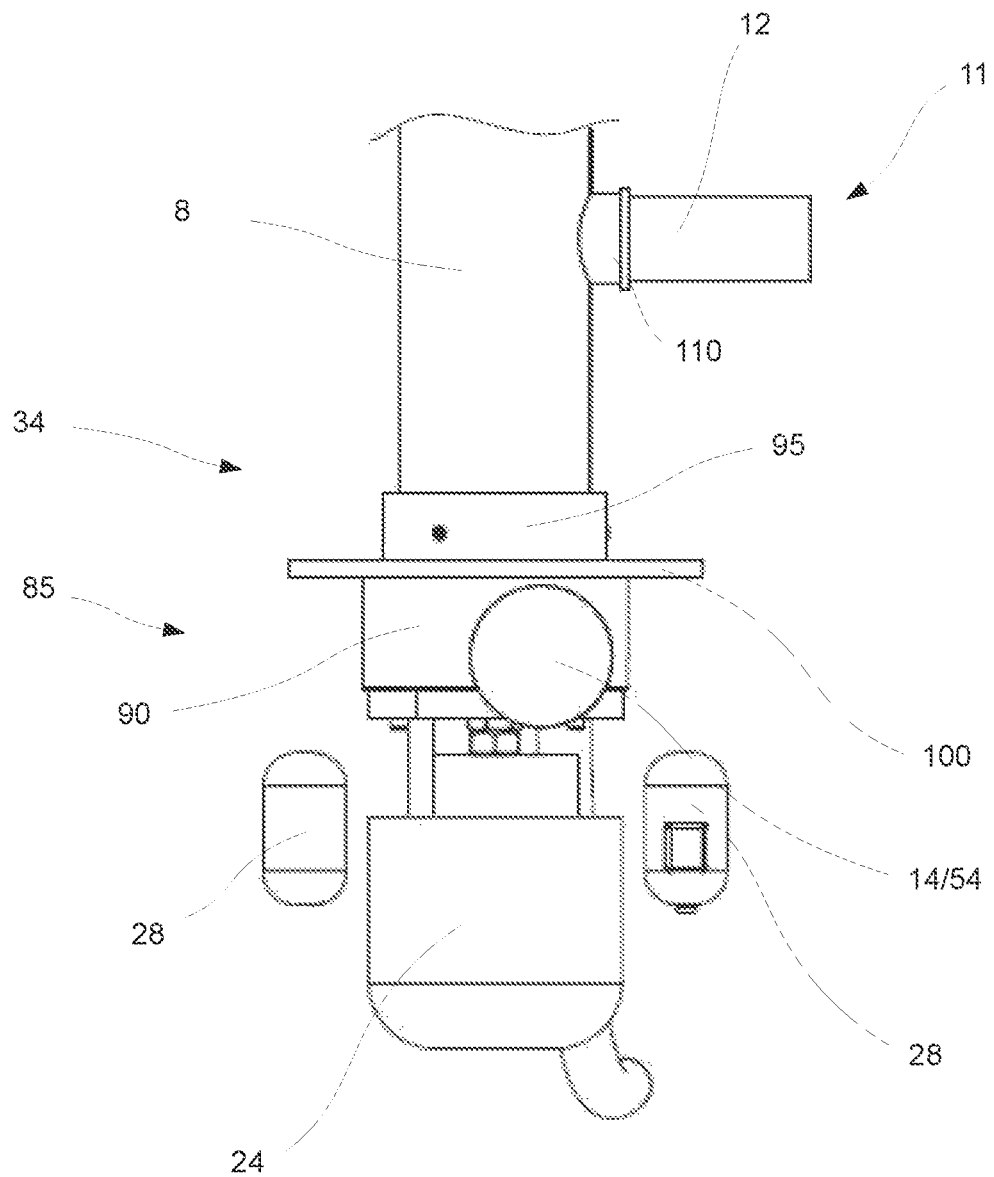
FIG. 6 shows a side view of the lower region of the chamber.

With reference to FIG. 3, FIG. 4, and FIG. 6, material to be dried is introduced into the chamber 8 by way of the feed assembly 11 which comprises a plunger feeding unit. In the form shown, the feed assembly 11 comprises a feed conduit 12 which is arranged in fluid communication with chamber 8 by way of collar 110 which seats within chamber wall 50. The skilled reader will understand that other arrangements for fluidly connecting the feed conduit 12 to chamber 8 will be known. It will be appreciated that the arrangement of the feed assembly 11 relative to the chamber 8 (ie. position) may vary depending on the specific drying application. The skilled reader will be aware of other arrangements which could be adapted to achieve an equivalent function, such as auger or extrusion arrangements. Thus, various feed mechanisms could be adapted for use to improve the current operational performance of the prototype apparatus described herein. Examples may include manual or automated/continuous feed mechanisms.

Figure 7:
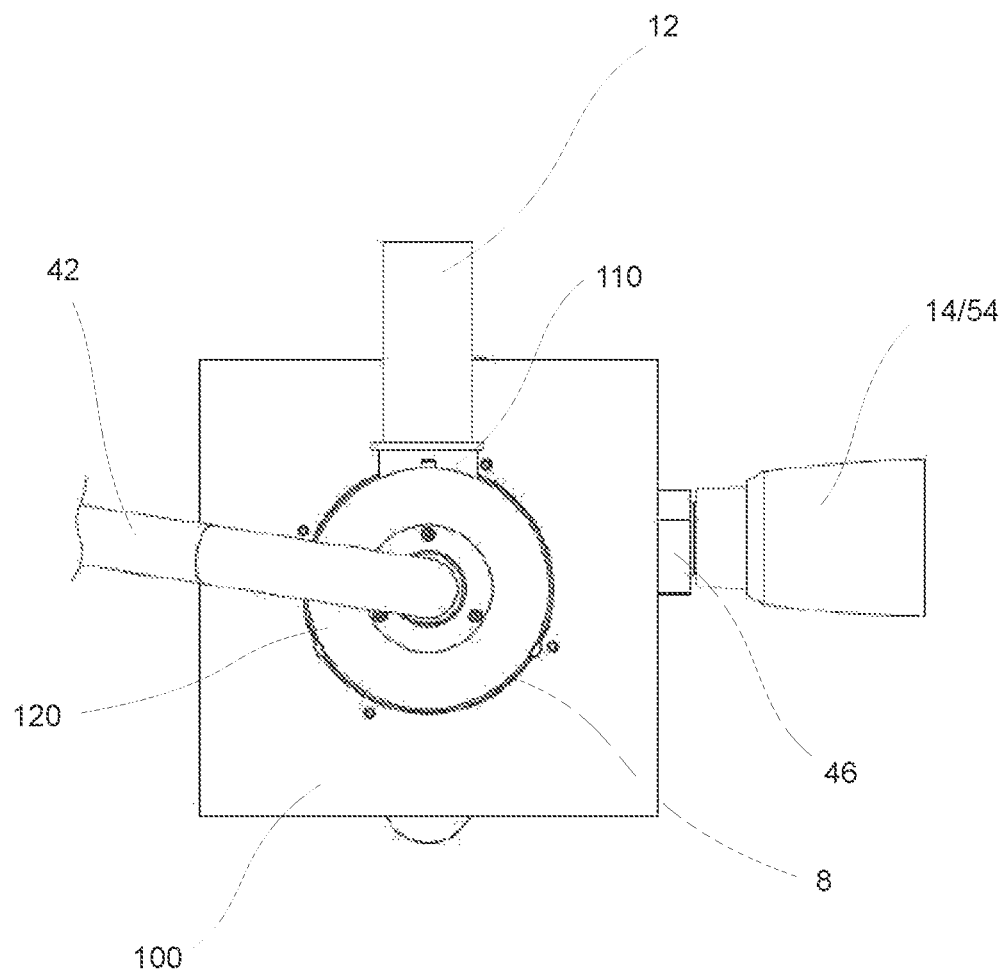
FIG. 7 shows a top view of the upper region of the chamber.
Figure 8:
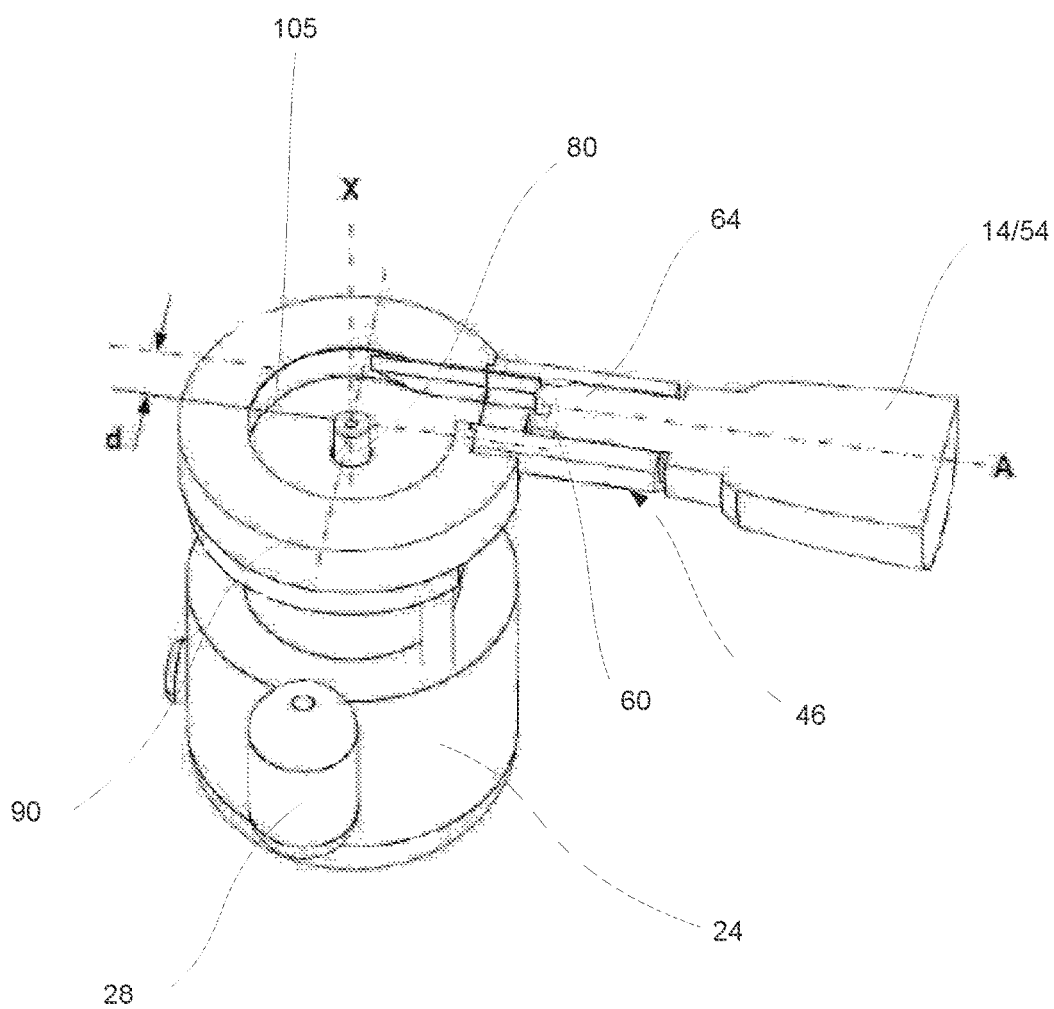
FIG. 8 shows a close up perspective view of a lower region of the chamber of the embodiment shown in FIG. 1 and FIG. 2, sectioned along a plane (a horizontal oriented plane in view of the embodiment shown) running through the longitudinal axis A.
Figure 9:
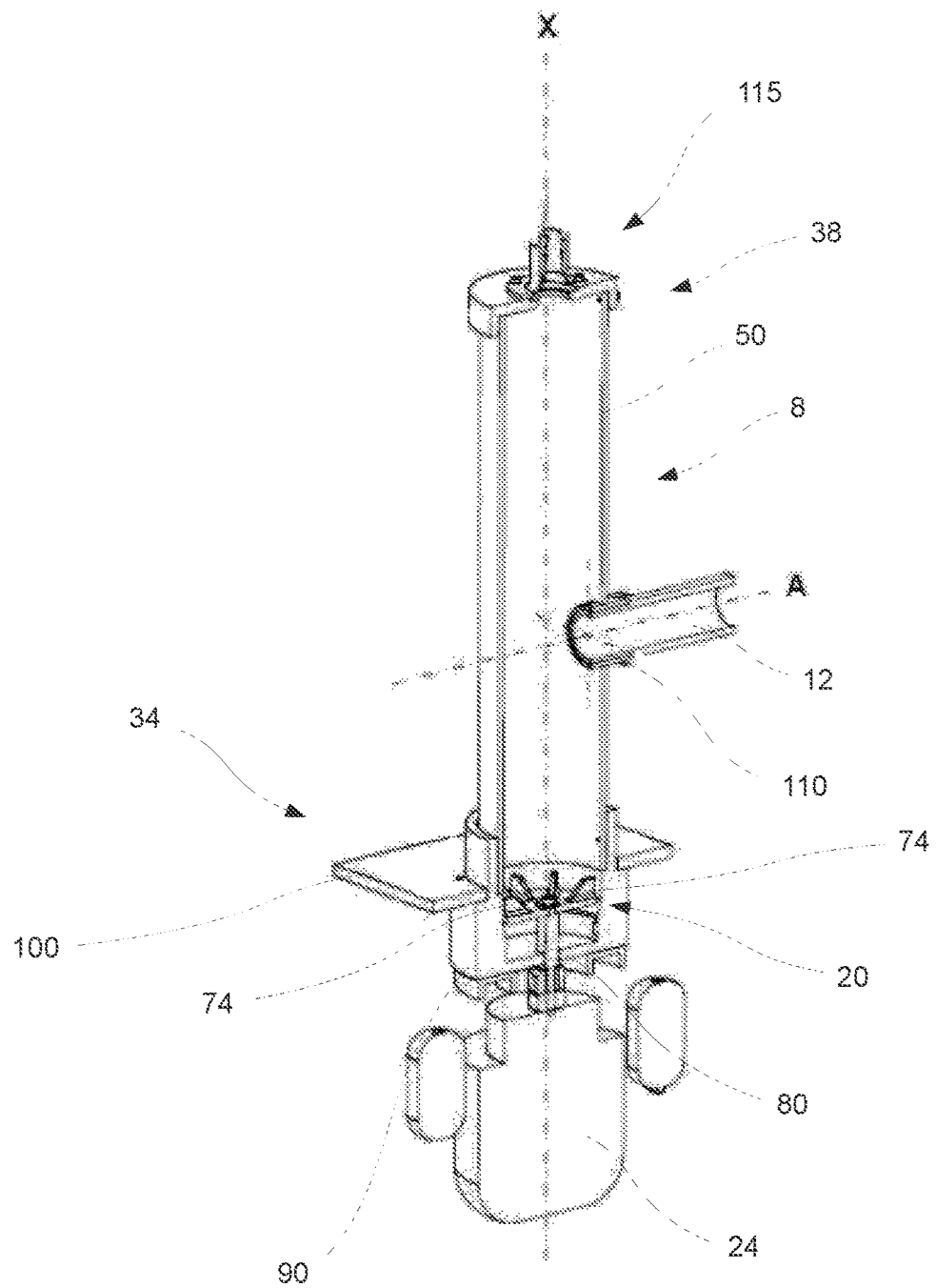
FIG. 9 shows a perspective view of the chamber, sectioned along its longitudinal axis.
Figure 10:
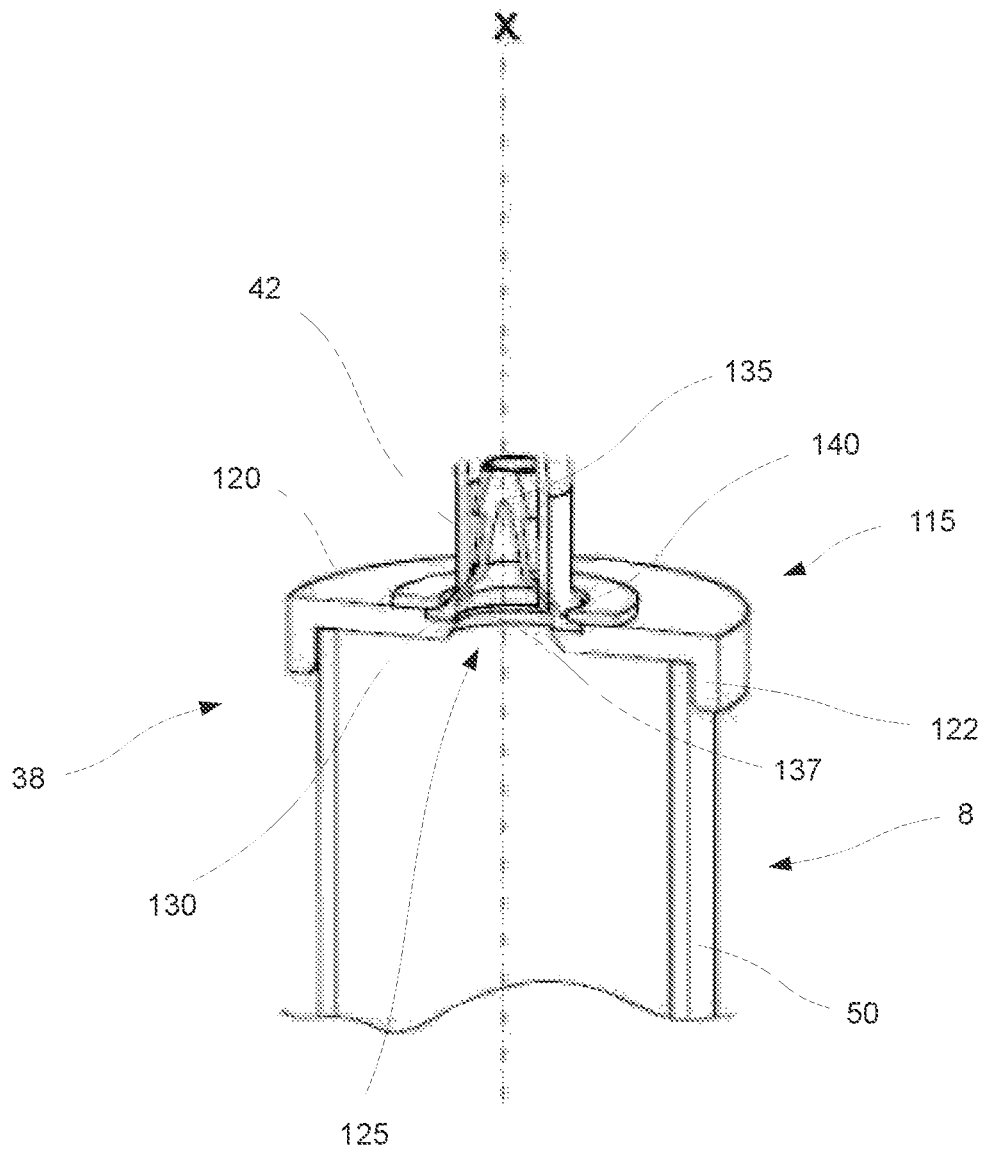
FIG. 10 shows a close up perspective view of an upper region of the chamber of the embodiment shown in FIG. 1 and FIG. 2, sectioned along its longitudinal axis.

With reference to FIG. 7 and FIG. 10, the second end 38 of the chamber 8 is closed by way of a closure assembly 115. The closure assembly 115 is provided in the form of a closure 120 which serves to provide a sealed fluid connection between conduit 42 and chamber 8. Particularly, closure 120 is of circular form having an annular flange 122 at its periphery which is appropriately dimensioned for receiving the free end (38) of chamber 8. The closure 120 further comprises a circular aperture 125 which provides a recessed seat 130 configured to support a base 137 of a nozzle 135, the nozzle providing a shaped region to which a free end of conduit 42 connects with. The base 137 of nozzle 135 is held in position by way of a retaining washer 140. As with the connection of the feed conduit 12 to chamber 8, the skilled reader will understand that other arrangements for fluidly connecting conduit 42 to chamber 8 for providing a substantially closed thermal environment could be developed.

In operation, substantially wet granular geological material to be dried is fed into chamber 8 by way of feed conduit 12 of feed assembly 11. Once introduced, the material is subject to the heated and generally rotational fluid flow provided within the chamber 8. In general, particulate having substantial moisture content will tend to gravitate toward the lower end (first end 34) of chamber 8 by way of gravity. As the particulate dries upon being subject to the oncoming heated fluid stream, it lightens in weight and becomes more susceptible to carriage by the moving air flow. Material not sufficiently dry will continue to fall by way of gravity toward the lowermost end 34 of chamber 8. If while continuing to fall the material dries sufficiently, its weight will reduce to the point at which it will be carried by the flow to the collection means 300. If not sufficiently dry, the material will continue to fall.

Non-sufficiently dry material may ultimately make contact with the impeller 20. In this event, the centripetal forces developed by the impeller 20 as it rotates will serve to cause the still moisture laden material to be directed radially outward from the centre axis of the impeller and toward the periphery (interior wall region) of the chamber 8 where the heated fluid flow engages the protrusions/fins 74 for mixing purposes. Thus, moist material again becomes exposed to the heated fluid flow for drying, where it is likely to be blown downstream (upwards into the chamber 8) by the relatively high flow velocities experienced proximal the periphery of the impeller 20. If not sufficiently dried/disaggregated/comminuted by the reiterated exposure, the material will again fall to the impeller 20, where it will be directed a further time to the periphery of the impeller 20 for another iteration of exposure to the heated fluid flow. It will be appreciated that, depending on the thermal environment desired, some portions of sample material may undergo a number of cycles of exposure to the heated fluid flow (and repeated contact with the impeller 20) before becoming sufficiently dry/disaggregated/comminuted to be susceptible for carriage by the flow to the collection means 300.

Furthermore, it will be appreciated that contact with the impeller 20 and protrusions 74 by falling material samples serves, at least in part, to break the sample up into smaller portions thereby increasing its effective surface area for drying purposes. In this manner, increasing the effective surface area of the sample portion has the effect of increasing the surface area of the material that is directly exposed to the heated environment, so reducing the drying time.

Additionally, larger particles or agglomerates may fall by way of gravity. The dryness of the sample material may, in some instances, likely not control whether the sample material falls or not. If the dried sample is sufficiently fine, it will flow through the system whether dry or not, but the rate of drying will be sufficiently high so that the sample material is dry by the time it is collected (or when leaving the chamber 8). Wetter sample material will tend to become agglomerated more readily meaning that larger heavier particles may be less influenced by the air flow.

Various performance parameters and associated results of a number of prototype tests are described below.

In one embodiment, the apparatus 2 may be provided in the form of a spin flash dryer arranged for receiving a wet (estimated up to about 30% moisture content) fine grained sticky mud and drying it to less than 1% moisture content within a short period of time (generally within a number of minutes or seconds) without raising the temperature of the material above the point where its mineralogy may change (at about 105 degrees Celsius).

Some embodiments of the apparatus described herein may find application to the drying of geological materials (soils, and drilling fines from diamond drilling) using a rugged and field portable system appropriate for use in the field at a remote drill site or similar.

Performance data of at least one test embodiment of the apparatus is as follows:

- Impeller (20) rotation about 22,000 revolutions per minute;
- 2.5 mm radial clearance between chamber (8) wall and impeller (20);
- 98.5 mm diameter spinning disc;
- rotor circumferential speed 111 m/s;
- air velocity at radial gap 212 m/s;
- air velocity in chamber, 0.5 m/s;
- air flow 2501 l/m.

In another prototype embodiment, testing using a meat grinder auger to feed wet material to the chamber (10 minute test run) with accurate dust collection and weighing, resulted in the following data:

Dry solid collected in separator: 94.91 g
Dry solid collected in chamber: 8.32 g
Dry solid collected below disc: 3.18 g
Total dry solid collected: 106.41 g
% of Total in separator: 89.19%
% of Total in chamber: 7.82%
% of Total below disc: 2.99%

In another prototype embodiment, testing using improved feed control accuracy, a plunger device, 10×10 g samples introduced into air flow chamber (8) in 1 min intervals (ie, a 10 minute feed period), and with 99% of dry solid accounted for, the following data was collected:

Wet sample total: 101.42 g Wet sample (MC): 29.99 g
Weight water: 30.41529 g Weight solid: 71.00471 g
Dry solid collected in separator: 70.06 g
Dry solid collected in chamber: 0.06 g
Dry solid collected below disc: 0.11 g
Total dry solid collected: 70.23 g
% of total in separator: 99.76%
% of total in chamber: 0.09%
% of total below disc: 0.16%
Missing solids: 0.77471 g
Missing %: 1.09%
Wet feed rate: 0.61 kg/hr
Evaporation rate: 0.18 kg/hr
Sample collection rate: 0.42 kg/hr In this test, the wet feed rate, evaporation rate and sample collection rate correspond to 10 grams/minute, 3 grams/minute, and 7 grams/minute respectively.

Further refinements of prototype embodiments have worked to increase efficiency allowing drying of, for example, in the order of about 150 g of material in about 2 to 3 minutes, with minimal material left remaining in the chamber (eg. <5 g). Such refinements have included favouring use of a plunger unit (over earlier used auger feed units) for introducing the material into the chamber 8 by allowing multiple, finer (eg. in the order or about 1 mm) streams. The plunger unit allows for a known quantity of sample material to be introduced into the chamber 8. In this manner, the size of the portion inserted by way of the plunger unit is balanced appropriately with respect to the size of the chamber 8 so as to ensure that the material inserted can be dried within an acceptable time frame and is of acceptable form (ie. preferably of a disagglomerated or disaggregated free flowing powder).

Those skilled in the art will appreciate that embodiments of the apparatus 2 described herein are susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

For example, the means of collecting the dried geological sample(s) is an area where improvement of the apparatus could be realised. In practice, the dried particulate may need to travel extended distances in order to be processed. Thus, conduit 42 could be reconfigured depending upon which transport mechanism is to be employed. Relevant pressure differentials and conduit forms are some of the variables which might require consideration if dried particulate needs to be transported across large distances.

Transport of the dried particulate from the chamber 8 could be adapted to improve system performance. As such, technologies could be employed to improve carriage velocities and volume to the collections means (300). Such systems could be configured to assist with appropriate temperature and pressure regulation of the thermal environment within which dried particulate is subject to during transport to the collection means. Additionally, such systems could be subject to manual or automated control technologies.

The chamber 8 may be arranged so as to reduce the risk of dried geological sample adhering to the internal surfaces of the chamber 8. In one embodiment, the chamber 8 could be arranged so as to be subject to a cyclical vibration which serves to 'shake' the chamber 8 during operation. This physical motion is considered desirable for assisting in the increase in yield of dried sample.

As noted, various materials or material coatings could be used to coat or line the internal surfaces of any of the internal components (such as for example, the internal surfaces of the chamber 8 and conduit 42, and the external surface of the impeller 20 and its fins 74) with the view to ensuring that dried sample does not inadvertently adhere to the surfaces. As one example, polytetrafluoroethylene (Teflon) was used to good effect to line the interior surface of the chamber 8.

As is clear from the principal aspects described above, various embodiments of methods for using the apparatus 2 (and prospective variations) can be readily performed for drying geological material. Furthermore, various embodiments of a system configured for use in drying geological material can be developed drawing from the principles of the operation of the invention described herein. Accordingly, such methods and systems are within the scope of the principles of the invention described herein.

Throughout this specification, and in the claims which follow, unless the context requires otherwise, the word "comprise" or variations such as "comprises" or "comprising", will be understood to imply the inclusion of a stated integer or group of integers but not the exclusion of any other integer or group of integers.

Furthermore, throughout the specification, unless the context requires otherwise, the word "include" or variations such as "includes" or "including", will be understood to imply the inclusion of a stated integer or group of integers but not the exclusion of any other integer or group of integers.

Additionally, where the terms "system", "device", and "apparatus" are used in the context of the invention, they are to be understood as including reference to any group of functionally related or interacting, interrelated, interdependent or associated components or elements that may be located in proximity to, separate from, integrated with, or discrete from, each other.

Modifications and variations such as would be apparent to a skilled addressee are deemed to be within the scope of the present invention.

The claims defining the invention are as follows:

1. A method for drying a sample of geological material having a substantial moisture content, the method comprising:

providing a flow of heated fluid for flowing through a passage from an upstream end toward an end downstream thereof, the flow of heated fluid being introduced into a portion of the passage in a tangential manner, and managing a thermal state of the flow of heated fluid so as to facilitate, in a rapid or expeditious manner, a reduction of the moisture content of a portion of the sample of material which becomes exposed to the flow of heated fluid while preserving one or more signature characteristics of the minerology of the portion.

2. The method according to claim 1, wherein the method comprises exposing the portion of the sample of geological material to the flow of heated fluid.

3. The method according to claim 1, wherein the thermal state of the flow of heated fluid is managed in a manner so as to facilitate a reduction of the moisture content of the portion of the portion of the sample to substantially below a predetermined level.

4. The method according to claim 1, wherein the managing of the thermal state of the heated fluid flow is performed so as to facilitate a substantial reduction of the moisture content of the portion of the sample while the temperature of the portion remains substantially below a predetermined temperature level.

5. The method according to claim 1, wherein the method includes facilitating or providing a low pressure region downstream of a fluid heating means so as to, at least in part, facilitate the flow of heated fluid.

6. The method according to claim 1, wherein providing the flow of heated fluid involves introducing a rotational, non-linear, or unsteady component of flow into the flow of heated fluid.

7. The method according to claim 1, wherein the method includes causing or facilitating the modification of the sample portion of material so as to increase its effective surface area, so providing for increased exposure of the sample of material, in its modified form, to the flow of heated fluid for drying purposes.

8. The method according to claim 1, wherein the method includes causing or facilitating repetitious exposure of portion(s) of the sample of material to the flow of heated fluid until sufficiently dry so as to be carried by the heated flow of fluid for collection purposes.

9. The method according to claim 1, wherein managing the thermal state of the flow of heated fluid comprises monitoring one or more physical characteristics of the fluid flow, including one or more of the following: fluid temperature, fluid flow velocity, or fluid pressure.

10. The method according to claim 1, wherein the method includes classifying the collected dried material into specific predetermined size ranges.

11. The method according to claim 1, wherein the temperature of the heated flow of fluid is managed so as to be below about 105 degrees Celsius.

12. The method according to claim 1, wherein the heated flow of fluid is managed so as to reduce the moisture content of the sample portion to below about 1 percent by weight.

13. The method according to claim 1, wherein operation of the method results in providing a disagglomerated or disaggregated free flowing powder.

14. The method according to claim 1, wherein the method comprises drying the material in discrete batches.

15. The method according to claim 1, wherein operation of the method provides from about 100 grams to about 200 grams of dried material in a time period of from about 2 minutes to 5 minutes, or from about 2 minutes to about 3 minutes.

16. The method according to claim 1, wherein the method can be performed at a remote location.

17. The method according to claim 1, wherein the method is part of an overarching method for the extraction and analysis of geological material performed at a remote location.

* * * * *

UNITED STATES PATENT AND TRADEMARK OFFICE
CERTIFICATE OF CORRECTION

PATENT NO. : 10,393,436 B2  
APPLICATION NO. : 15/528377  
DATED : August 27, 2019  
INVENTOR(S) : David Charles Lawie, Anthony Malcolm Stevens and Frederick Allan Blaine Page 1 of 1

It is certified that error appears in the above-identified patent and that said Letters Patent is hereby corrected as shown below:

In the Claims

Claim 3, Column 31, Line 7, replace "portion of the portion of the sample" with "portion of the sample"

Signed and Sealed this
First Day of October, 2019

Andrei Iancu
*Director of the United States Patent and Trademark Office*